(12) United States Patent
Okumura et al.

(10) Patent No.: US 7,109,278 B2
(45) Date of Patent: Sep. 19, 2006

(54) ORGANOMETALLIC TRANSITION METAL COMPOUND, BISCYCLOPENTADIENYL LIGAND SYSTEM, CATALYST SYSTEM AND PREPARATION OF POLYOLEFINS

(75) Inventors: Yoshikuni Okumura, Kanagawa (JP); Markus Oberhoff, Drensteinfurt (DE); Jörg Schottek, Idstein-Wörsdorf (DE); Jörg Schulte, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/496,142

(22) PCT Filed: Nov. 26, 2002

(86) PCT No.: PCT/EP02/13296

§ 371 (c)(1),
(2), (4) Date: May 20, 2004

(87) PCT Pub. No.: WO03/045551

PCT Pub. Date: Jun. 5, 2003

(65) Prior Publication Data

US 2004/0260107 A1 Dec. 23, 2004

(30) Foreign Application Priority Data

Nov. 30, 2001 (DE) ................ 101 58 656

(51) Int. Cl.
| C08F 4/64 | (2006.01) |
| C08F 4/72 | (2006.01) |
| C07F 17/00 | (2006.01) |
| B01J 31/38 | (2006.01) |

(52) U.S. Cl. .............. 526/170; 526/160; 526/941; 526/943; 526/172; 526/161; 556/11; 556/53; 556/51; 502/103

(58) Field of Classification Search ........... 556/51–53; 526/160, 170, 941, 943; 521/943; 502/103
See application file for complete search history.

(56) References Cited

U.S. PATENT DOCUMENTS 5,998,039 A * 12/1999 Tanizaki et al. ......... 428/516

(Continued)

FOREIGN PATENT DOCUMENTS

| DE | 199 62 905 A1 * | 7/2001 |
| EP | 834 519 | 4/1998 |
| EP | 834 519 A1 * | 4/1998 |
| WO | 91/09882 | 7/1991 |
| WO | 96/00243 | 1/1996 |

(Continued)

OTHER PUBLICATIONS

Kajigaeshi et al., Bull.Chem. Soc., Japan, 62, 439 (1989).
Pat. Abst. Japan, 11349618.
Pat. Abst. Japan, 11349617.

Primary Examiner—David W. Wu
Assistant Examiner—Rip A. Lee
(74) Attorney, Agent, or Firm—Novak Druce & Quigg, LLP; Jason D. Voight

(57) ABSTRACT

Organometallic transition metal compounds of the formula (I) where $M^1$ is an element of group 3, 4, 5 or 6 of the Periodic Table of the Elements or the lanthanides; X are identical or different and are each halogen, hydrogen, $C_1$–$C_{20}$-alkyl, $C_2$–$C_{20}$-alkenyl, $C_6$–$C_{22}$-aryl, alkylaryl or arylalkyl having from 1 to 10 carbon atoms in the alkyl part and from 6 to 22 carbon atoms in the aryl part, —$OR^5$ or —$NR^5R^6$, where two radicals X may also be joined to one another or two radicals X may together form a substituted or unsubstituted diene ligand, in particular a 1,3-diene ligand; where $R^5$ and $R^6$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 22 carbon atoms in the aryl radical; n is a natural number from 1 to 4 which is equal to the oxidation number of $M^1$ minus 2; $R^1$ is a $C_2$–$C_{40}$ radical which is branched in the α position; $R^2$ is hydrogen or a $C_1$–$C_{40}$ radical which may be branched or unbranched in the α position; $R^3$, $R^{3a}$ and $R^{3b}$ are identical or different and are each hydrogen or a $C_1$–$C_{40}$ radical, where at least one of the radicals $R^3$, $R^{3a}$, $R^{3b}$ is not hydrogen; $R^4$ is a substituted or unsubstituted $C_6$–$C_{40}$-aryl radical or $C_2$–$C_{40}$-heteroaromatic radical containing at least one heteroatom selected from the group consisting of O, N, S and P; T is a divalent $C_1$–$C_{40}$ group which together with the cyclopentadienyl ring forms a further saturated or unsaturated ring system having a ring size of from 5 to 12 atoms, where T may contain the heteroatoms Si, Ge, N, P, O or S withing the ring system fused onto the cyclopentadienyl ring; and Z is a bridge consisting of a divalent atom or a divalent group, can be used in catalyst systems for preparing polyolefins by polymerization or copolymerization of at least one olefin. Biscyclopentadienyl ligand systems which have such a substitution pattern and can be used for preparing these organometallic transition metal compounds are also provided

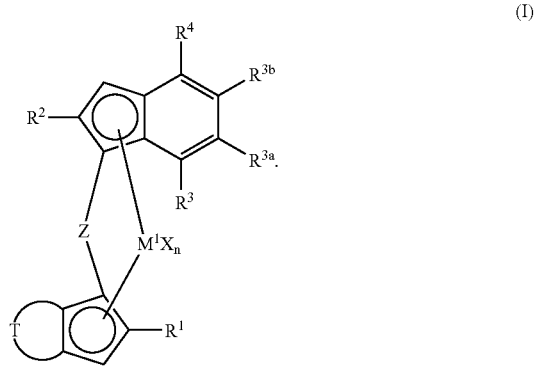

11 Claims, No Drawings

U.S. PATENT DOCUMENTS

| | | | |
|---|---|---|---|
| 6,444,606 B1 | 9/2002 | Bingel et al. | 502/152 |
| 6,552,210 B1 | 4/2003 | Göres et al. | |
| 6,583,238 B1 | 6/2003 | Göres et al. | |
| 6,589,905 B1 | 7/2003 | Fischer et al. | 502/300 |
| 2003/0130443 A1 | 7/2003 | Suhm et al. | |
| 2003/0199703 A1 | 10/2003 | Schulte et al. | |

FOREIGN PATENT DOCUMENTS

| | | |
|---|---|---|
| WO | 98/40419 | 9/1998 |
| WO | 99/06414 | 2/1999 |
| WO | 99/50274 | 10/1999 |
| WO | 99/50312 | 10/1999 |
| WO | 00/05277 | 2/2000 |
| WO | 00/20426 | 4/2000 |
| WO | 00/20462 | 4/2000 |
| WO | WO 00/44799 A1 * | 8/2000 |
| WO | 01/46274 | 6/2001 |
| WO | 01/48034 | 7/2001 |
| WO | 0158970 | 8/2001 |
| WO | 02/02575 | 1/2002 |
| WO | 02/02576 | 1/2002 |
| WO | 02/18397 | 3/2002 |
| WO | 02/90399 | 11/2002 |
| WO | 02/96920 | 12/2002 |
| WO | 03/002583 | 1/2003 |

* cited by examiner

ORGANOMETALLIC TRANSITION METAL COMPOUND, BISCYCLOPENTADIENYL LIGAND SYSTEM, CATALYST SYSTEM AND PREPARATION OF POLYOLEFINS

The present invention relates to organometallic transition metal compounds of the formula (I)

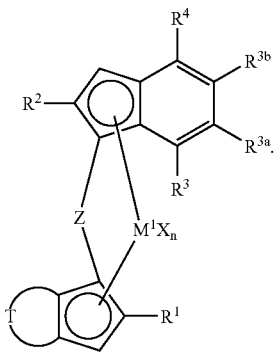

(I)

where
$M^1$ is an element of group 3, 4, 5 or 6 of the Periodic Table of the Elements or the lanthanides, X are identical or different and are each halogen, hydrogen, $C_1$–$C_{20}$-alkyl, $C_2$–$C_{20}$-alkenyl, $C_6$–$C_{22}$-aryl, alkylaryl or arylalkyl having from 1 to 10 carbon atoms in the alkyl part and from 6 to 22 carbon atoms in the aryl part, —$OR^5$ or —$NR^5R^6$, where two radicals X may also be joined to one another or two radicals X may together form a substituted or unsubstituted diene ligand, in particular a 1,3-diene ligand, where
  $R^5$ and $R^6$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 22 carbon atoms in the aryl radical, n is a natural number from 1 to 4 which is equal to the oxidation number of $M^1$ minus 2, $R^1$ is a $C_2$–$C_{40}$ radical which is branched in the α position, $R^2$ is hydrogen or a $C_1$–$C_{40}$ radical which may be branched or unbranched in the α position, $R^3$, $R^{3a}$ and $R^{3b}$ are identical or different and are each hydrogen or a $C_1$–$C_{40}$ radical, where at least one of the radicals $R^3$, $R^{3a}$ and $R^{3b}$ is not hydrogen, $R^4$ is a substituted or unsubstituted $C_6$–$C_{40}$-aryl radical or $C_2$–$C_{40}$-heteroaromatic radical containing at least one heteroatom selected from the group consisting of O, N, S and P, T is a divalent $C_1$–$C_{40}$ group which together with the cyclopentadienyl ring forms a further saturated or unsaturated ring system having a ring size of from 5 to 12 atoms, where T may contain the heteroatoms Si, Ge, N, P, O or S within the ring system fused onto the cyclopentadienyl ring,
and Z is a bridge consisting of a divalent atom or a divalent group.

In addition, the present invention provides biscyclopentadienyl ligand systems having a substitution pattern of this type, catalyst systems comprising at least one of the organometallic transition metal compounds of the present invention, a process for preparing polyolefins by polymerization or copolymerization of at least one olefin in the presence of one of the catalyst systems of the present invention and the use of the biscyclopentadienyl ligand systems of the present invention for preparing organometallic transition metal compounds.

Research and development on the use of organometallic transition metal compounds, in particular metallocenes, as catalyst components for the polymerization and copolymerization of olefins with the objective of producing tailored polyolefins has been carried out actively in universities and in industry over the past 15 years.

Now, not only the ethylene-based polyolefins prepared by means of metallocene catalyst systems but also, in particular, propylene-based polyolefins prepared by means of metallocene catalyst systsems represent a market segment displaying dynamic growth.

In the preparation of propylene-ethylene copolymers which are employed, for example, as "rubber phase" in the preparation of impact-modified propylene polymers, a problem which is usually encountered is that the molar masses of the propylene-ethylene copolymer which can be achieved using the known metallocene catalysts are significantly reduced compared to the molar masses of the isotactic propylene homopolymer.

EP-A-834519 describes catalyst systems comprising C1-symmetric bisindenyl-metallocenes which are suitable for the homopolymerization of propylene and produce propylene homopolymers having high melting points.

WO 01/48034 describes catalyst systems which, owing to specifically substituted metallocenes, are able to produce both propylene-ethylene copolymers as rubber phase having a sufficient molar mass and propylene homopolymers having a sufficiently high melting point for satisfactory stiffness of the matrix.

However, the known metallocene catalyst systems leave something to be desired in respect of the combination of high molar mass of the rubber phase and stiffness of the matrix.

It is an object of the present invention to find organometallic transition metal compounds which when used as catalyst constituents are able to further increase, compared to the known metallocenes, the molar mass of the propylene-ethylene copolymer resulting from the polymerization and at the same time maintain the desired stiffness of the propylene homopolymer.

We have found that this object is achieved by the organometallic transition metal compounds of the formula (I) mentioned at the outset.

$M^1$ is an element of groups 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium, hafnium, particularly preferably zirconium or hafnium, and very particularly preferably zirconium.

The radicals X are identical or different, preferably identical, and are each halogen, for example fluorine, chlorine, bromine, iodine, preferably chlorine, hydrogen, $C_1$–$C_{20}$-alkyl, preferably $C_1$–$C_4$-alkyl, $C_2$–$C_{20}$-alkenyl, preferably $C_2$–$C_4$-alkenyl, $C_6$–$C_{22}$-aryl, preferably $C_6$–$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part, —$OR^5$ or —$NR^5R^6$, preferably —$OR^5$, where two radicals X may also be joined to one another, preferably two radicals —$OR^5$. Two radicals X may also together form a substituted or unsubstituted diene ligand, in particular a 1,3-diene ligand, where the radicals $R^5$ and $R^6$ are each $C_1$–$C_{10}$-alkyl, preferably $C_1$–$C_4$-alkyl, $C_6$–$C_{15}$-aryl, preferably $C_6$–$C_{10}$- aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical.

Unless restricted further, alkyl is a linear, branched or cyclic radical such as methyl, ethyl, n-propyl, isopropyl, n-butyl, i-butyl, s-butyl, t-butyl, n-pentyl, cyclopentyl, n-hexyl, cyclohexyl, n-heptyl or n-octyl.

The index n is a natural number from 1 to 4 which is equal to the oxidation number of $M^1$ minus 2, and is preferably 2 for the elements of group 4 of the Periodic Table of the Elements.

The radical $R^1$ is a $C_2$–$C_{40}$ radical which is branched in the α position. For the present purposes, a radical branched in the α position is a radical whose linking α atom bears at least two directly bound atoms which are different from hydrogen and not more than one directly bound hydrogen atom. The linking α atom is preferably carbon. The radical $R^1$ is particularly preferably $C_3$–$C_{20}$-alkyl, preferably $C_3$–$C_8$-alkyl, $C_3$–$C_{20}$-alkenyl, preferably $C_3$–$C_8$-alkenyl, $C_6$–$C_{22}$-aryl, preferably $C_6$–$C_{10}$-aryl, alkylaryl, arylalkyl or arylalkenyl having from 1 to 10, preferably from 1 to 4, carbon atoms in the alkyl part and from 6 to 22, preferably from 6 to 10, carbon atoms in the aryl part, $C_3$–$C_{12}$-cycloalkyl, preferably $C_5$–$C_8$-cycloalkyl, or cycloalkenyl, or the radical $R^1$ is a saturated or unsaturated heterocycle containing from 3 to 10 carbon atoms and at least one heteroatom selected from the group consisting of O, N, S, P and Si, preferably O, N and S, where the carbocycle or the heterocycle may be substituted by further radicals $R^7$, with $R^7$ being defined as for $R^3$ and a plurality of radicals $R^7$ being able to be identical or different. Examples of preferred radicals $R^1$ are isopropyl, cyclobutyl, 1-methylpropyl, 1-methylbutyl, 1-ethylbutyl, 1-methylpentyl, cyclopentyl, cyclohexyl, t-butyl, cyclopent-2-enyl, cyclopent-3-enyl, cyclohex-2-enyl, cyclohex-3-enyl, para-methylcyclohexyl, diphenylmethyl, triphenylmethyl, phenyl, 2-tolyl, 3-tolyl, 4-tolyl, 2,6-dimethylphenyl, 2,4,6-trimethylphenyl, 1-naphthyl, 2-naphthyl, phenanthyl, furyl, thienyl, 2-(5-methylfuryl), 2-(5-methylthienyl), trifluoromethyl and trimethylsilyl, in particular isopropyl, 1-methylpropyl, 1-methylbutyl, 1-ethylbutyl, 1-methylpentyl and cyclohexyl.

The radical $R^2$ can be identical to or different from $R^1$, preferably different from $R^1$, and is hydrogen or a $C_1$–$C_{40}$ radical which may be branched or unbranched in the α position. The radical $R^2$ is preferably hydrogen or a $C_1$–$C_{40}$-hydrocarbon radical which is unbranched in the α position and whose linking α atom is connected to no more than one atom different from hydrogen. The linking α atom is preferably a carbon atom. The radical $R^2$ is particularly preferably an unbranched $C_1$–$C_{20}$-alkyl, preferably $C_1$–$C_8$-alkyl, radical, a $C_2$–$C_{20}$-alkenyl, preferably $C_2$–$C_8$-alkenyl, radical, an arylalkyl radical having from 1 to 10, preferably from 1 to 4 carbon atoms in the alkyl part and from 6 to 22, preferably from 6 to 10, carbon atoms in the aryl part. Examples of very particularly preferred radicals $R^2$ are hydrogen, methyl, ethyl, n-propyl, n-butyl, i-butyl, n-pentyl, benzyl and 2-phenylethyl.

The radicals $R^3$, $R^{3a}$ and $R^{3b}$ are identical or different and are each hydrogen or a $C_1$–$C_{20}$ radical, for example a $C_1$–$C_{20}$-alkyl, preferably $C_1$–$C_4$-alkyl, radical, a $C_2$–$C_{20}$-alkenyl, preferably $C_2$–$C_4$-alkenyl, radical, a $C_6$–$C_{22}$-aryl, preferably $C_6$–$C_{10}$-aryl, radical, an alkylaryl or arylalkyl radical having from 1 to 10, preferably from 1 to 4 carbon atoms in the alkyl part and from 6 to 22, preferably from 6 to 10 carbon atoms in the aryl part, where the radicals may also be halogenated and at least one of the radicals $R^3$, $R^{3a}$ and $R^{3b}$, in particular $R^3$, is not hydrogen. It is preferred that $R^3$ or $R^{3a}$ is not hydrogen and very particularly preferred that $R^3$ is not hydrogen. Examples of particularly preferred radicals $R^3$, $R^{3a}$ and $R^{3b}$ are hydrogen, methyl, ethyl, n-propyl, isopropyl, t-butyl, trifluoromethyl, phenyl, 4-tolyl, 3,5-dimethylphenyl, 3,5-di(tert-butyl)phenyl, p-tert-butylphenyl and 1-naphthyl.

The radical $R^4$ is a substituted or unsubstituted $C_6$–$C_{40}$-aryl radical or a $C_2$–$C_{40}$-heteroaromatic radical containing at least one heteroatom selected from the group consisting of O, N, S and P. The radical $R^4$ is preferably a substituted or unsubstituted $C_6$–$C_{40}$-aryl radical having from 1 to 10, preferably from 1 to 4, carbon atoms in any alkyl substituent and preferably from 6 to 22, more preferably from 6 to 10 carbon atoms in the aryl part, where the radicals may also be halogenated. Examples of preferred radicals $R^4$ are phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthrenyl, p-isopropylphenyl, p-tert-butylphenyl, p-s-butylphenyl, p-cyclohexylphenyl and p-trimethylsilylphenyl.

Since the interplay between the steric effects of the radicals $R^1$, $R^2$, $R^3$, $R^{3a}$, $R^{3b}$ and $R^4$, in particular the radicals $R^1$, $R^2$, $R^3$, $R^{3a}$ and $R^4$, is particularly critical in determining the polymerization properties of the organometallic transition metal compounds of the present invention, functional groups on the radicals described usually do not have a critical influence on the fundamental polymerization behavior of the organometallic transition metal compounds, as long as these functional groups are chemically inert under the polymerization conditions.

T is a divalent $C_1$–$C_{40}$ group which together with the cyclopentadienyl ring forms a further saturated or unsaturated ring system which has a ring size of from 5 to 12, preferably from 5 to 7, particularly preferably 5 or 6, atoms, where T may contain the heteroatoms Si, Ge, N, P, O or S, preferably N or S, within the ring system fused onto the cyclopentadienyl ring.

Z is a bridge consisting of a divalent atom or a divalent group. Examples of Z are:

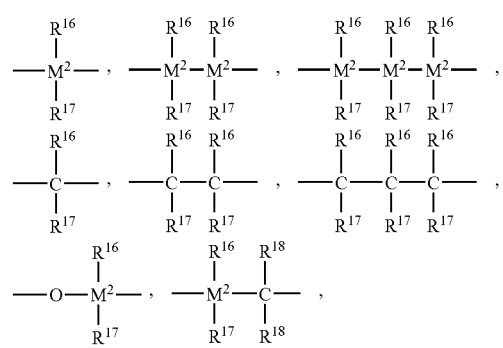

$=BR^{16}$, $=BNR^{16}R^{17}$, $=AlR^{16}$, —O—, —S—, $=SO$, $=SO_2$, $=NR^{16}$, $=CO$, $=PR^{16}$ or $=P(O)R^{16}$, preferably

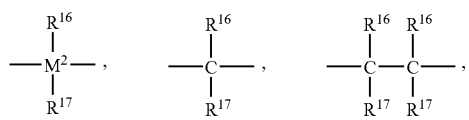

where $M^2$ is silicon, germanium or tin, preferably silicon or gernamium, particularly preferably silicon, and $R^{16}$, $R^{17}$ and $R^{18}$ are identical or different and are each a hydrogen atom, a halogen atom, a trimethylsilyl group, a $C_1$–$C_{10}$-alkyl, preferably $C_1$–$C_3$-alkyl, group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy, preferably $C_1$–$C_3$-alkoxy, group, a $C_7$–$C_{15}$-alkylaryloxy group, a $C_2$–$C_{10}$-alkenyl, preferably $C_2$–$C_4$-alkenyl, group, a $C_7$–$C_{40}$-arylalkyl group, a $C_8$–$C_{40}$-arylalkenyl group or a $C_7$–$C_{40}$-alkylaryl group or two adjacent radicals together with the atoms connecting them form a saturated or unsaturated ring having from 4 to 15 carbon atoms.

$R^{16}$, $R^{17}$ and $R^{18}$ are preferably identical or different $C_1$–$C_4$-alkyl groups, in particular methyl or ethyl or phenyl groups.

Particularly preferred embodiments of Z are the bridges: dimethylsilanediyl, methylphenylsilanediyl, diphenylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene and diphenylmethylidene, in particular dimethylsilanediyl, diphenylsilanediyl and ethylidene.

Preference is given to organometallic transition metal compounds of the formula (I) in which $M^1$ is an element of group 4 of the Periodic Table of the Elements, n is 2, $R^3$, $R^{3a}$ are identical or different and are each hydrogen or a $C_1$–$C_{40}$ radical, where at least one of the radicals $R^3$ and $R^{3a}$ is not hydrogen, $R^{3b}$ is hydrogen, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under the formula (I).

$M^1$ is preferably zirconium or hafnium, particularly preferably zirconium.

The radicals $R^3$ and $R^{3a}$ are identical or different and are each hydrogen or a $C_1$–$C_{40}$ radical, for example a $C_1$–$C_{20}$-alkyl, preferably $C_1$–$C_4$-alkyl, radical, a $C_2$–$C_{20}$-alkenyl, preferably $C_2$–$C_4$-alkenyl, radical, a $C_6$–$C_{22}$-aryl, preferably $C_6$–$C_{10}$-aryl, radical, an alkylaryl or arylalkyl radical having from 1 to 10, preferably from 1 to 4, carbon atoms in the alkyl part and from 6 to 22, preferably from 6 to 10 carbon atoms in the aryl part, where the radicals may also be halogenated and at least one, preferably precisely one, of the radicals $R^3$ and $R^{3a}$ is not hydrogen. Preference is given to $R^3$ being different from hydrogen and $R^{3a}$ being hydrogen.

$R^3$ and $R^{3a}$ are preferably different and are each hydrogen, a $C_1$–$C_4$-alkyl radical, a $C_6$–$C_{10}$-aryl radical or an alkylaryl radical which preferably has from 1 to 4 carbon atoms in the alkyl radical and 6 carbon atoms in the aryl radical.

Examples of particularly preferred radicals $R^3$ are methyl, ethyl, n-propyl, isopropyl, t-butyl, phenyl, 4-tolyl, 3,5-dimethylphenyl, 3,5-di(tert-butyl)phenyl, p-tert-butylphenyl and 1-naphthyl, and examples of particularly preferred radicals $R^{3a}$ are hydrogen, phenyl, 4-tolyl, 3,5-dimethylphenyl, 3,5-di(tert-butyl)phenyl, p-tert-butylphenyl and 1-naphthyl.

T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring. T is preferably a substituted or unsubstituted butadienylene group of the type —C($R^{4'}$)=C($R^8$)—C($R^8$)=C($R^8$)—, a —C($R^8$)=C($R^8$)—S— group or a —N($R^8$)—C($R^8$)=C($R^8$)— group, where $R^{4'}$ and $R^8$ are identical or different and are as defined for $R^3$ or $R^4$ or $R^{4'}$ and $R^8$ or two radicals $R^8$ together form a saturated or unsaturated, preferably an unsaturated, 5- to 7-membered ring system.

Also preference is given to organometallic transition metal compounds of the formula (I) in which $M^1$ is an element of group 4 of the Periodic Table of the Elements, n is 2, $R^3$ is a $C_1$–$C_{40}$ radical, $R^{3a}$, $R^{3b}$ are identical or different and are each hydrogen or a $C_1$–$C_{40}$ radical, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under the formula (1).

$M^1$ is preferably zirconium or hafnium, particularly preferably zirconium.

$R^3$ is a $C_1$–$C_{40}$ radical, for example a $C_1$–$C_{20}$-alkyl, preferably $C_1$–$C_4$-alkyl, radical, a $C_2$–$C_{20}$-alkenyl, preferably $C_2$–$C_4$-alkenyl, radical, a $C_6$–$C_{22}$-aryl, preferably $C_6$–$C_{10}$-aryl, radical, an alkylaryl or arylalkyl radical, preferably an alkylaryl radical, having from 1 to 10, preferably from 1 to 4, carbon atoms in the alkyl part and from 6 to 22, preferably from 6 to 10 carbon atoms, particularly preferably 6 carbon atoms in the aryl part, where the radicals may also be halogenated.

The radicals $R^{3a}$ and $R^{3b}$ are identical or different and are each hydrogen or a $C_1$–$C_{40}$ radical, for example a $C_1$–$C_{20}$-alkyl, preferably $C_1$–$C_4$-alkyl, radical, a $C_2$–$C_{20}$-alkenyl, preferably $C_2$–$C_4$-alkenyl, radical, a $C_6$–$C_{22}$-aryl, preferably $C_6$–$C_{10}$-aryl, radical, an alkylaryl or arylalkyl radical, preferably an alkylaryl radical, having from 1 to 10, preferably from 1 to 4, carbon atoms in the alkyl part and from 6 to 22, preferably from 6 to 10 carbon atoms, particularly preferably 6 carbon atoms in the aryl part, where the radicals may also be halogenated.

Examples of particularly preferred radicals $R^3$ are methyl, ethyl, n-propyl, isopropyl, t-butyl, phenyl, 4-tolyl, 3,5-dimethylphenyl, 3,5-di(tert-butyl)phenyl, p-tert-butylphenyl and 1-naphthyl, and examples of particularly preferred radicals $R^{3a}$ are hydrogen, phenyl, 4-tolyl, 3,5-dimethylphenyl, 3,5-di(tert-butyl)phenyl, p-tert-butylphenyl and 1-naphthyl.

T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring. T is preferably a substituted or unsubstituted butadienylene group of the type —C(R$^{4'}$)=C(R$^8$)—C(R$^8$)=C(R$^8$)—, a —C(R$^8$)=C(R$^8$)—S— group or a —N(R$^8$)—C(R$^8$)=C(R$^8$)— group, where R$^{4'}$ and R$^8$ are identical or different and are as defined for R$^3$ or R$^4$ or R$^{4'''}$ and R$^8$ or two radicals R$^8$ together form a saturated or unsaturated, preferably an unsaturated, 5- to 7-membered ring system.

Particular preference is given to organometallic transition metal compounds in which the formula (I) corresponds to the formula (Ia), (Ib) or (Ic),

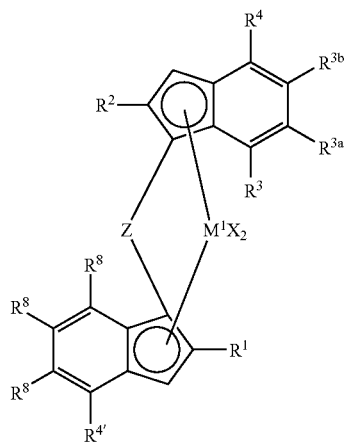

(Ia)

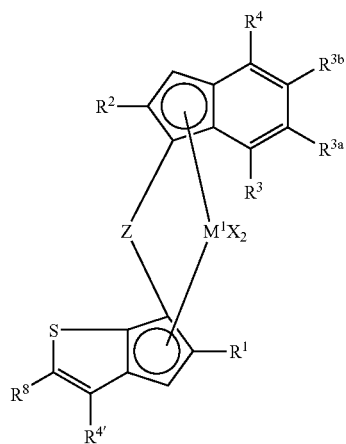

(Ib)

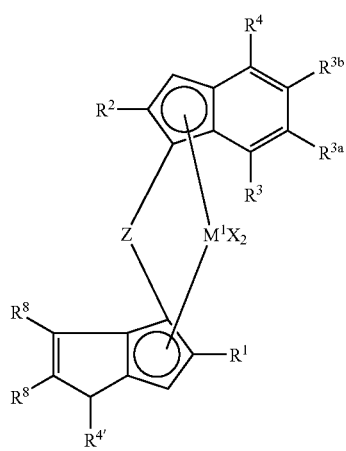

(Ic)

in which
M$^1$ is an element of group 4 of the Periodic Table of the Elements,
X are identical or different and are each halogen, C$_1$–C$_4$-alkyl, benzyl or OR$^5$, where R$^5$ is a C$_6$–C$_{10}$-aryl radical or a C$_7$–C$_{14}$-alkylaryl radical, in each case preferably having from 1 to 4 carbon atoms in the alkyl radical and 6 carbon atoms in the aryl radical, and two radicals R$^5$ may be joined to one another,
R$^3$, R$^{3a}$ and R$^{3b}$ are identical or different and are each hydrogen or a C$_1$–C$_{40}$ radical, where at least one of the radicals R$^3$, R$^{3a}$ or R$^{3b}$ is not hydrogen,
R$^{4'}$, R$^8$ are identical or different and are as defined for R$^3$ or R$^4$, or R$^{4'}$ and R$^8$ or two radicals R$^8$ together form a saturated or unsaturated, preferably unsaturated, 5- to 7-membered ring system,
Z is a bridge of the type SiR$^{16}$R$^{17}$, CR$^{16}$R$^{17}$ or C$_2$H$_4$, where R$^{16}$ and R$^{17}$ are identical or different and are each methyl, ethyl or phenyl, and
R$^1$, R$^2$ and R$^4$ are as defined under formula I.

M$^1$ is an element of group 4 of the Periodic Table of the Elements, preferably zirconium or hafnium, particularly preferably zirconium.

The radicals R$^3$, R$^{3a}$ and R$^{3b}$ are identical or different and are each hydrogen or a C$_1$–C$_{40}$ radical, for example a C$_1$–C$_{20}$-alkyl, preferably C$_{1-4}$-alkyl, radical, a C$_2$–C$_{20}$-alkenyl, preferably C$_2$–C$_4$-alkenyl, radical, a C$_6$–C$_{22}$-aryl, preferably C$_6$–C$_{10}$-aryl, radical, an alkylaryl or arylalkyl radical having from 1 to 10, preferably from 1 to 4, carbon atoms in the alkyl part and from 6 to 22, preferably from 6 to 10, carbon atoms in the aryl part, where the radicals may also be halogenated and at least one of the radicals R$^3$, R$^{3a}$ or R$^{3b}$ is not hydrogen. Preference is given to R$^3$ being different from hydrogen.

R$^{3a}$ and R$^{3b}$ are preferably hydrogen, a C$_1$–C$_4$-alkyl radical, a C$_6$–C$_{10}$-aryl radical or an alkylaryl radical which preferably has from 1 to 4 carbon atoms in the alkyl part and 6 carbon atoms in the aryl part.

Examples of particularly preferred radicals R$^3$ are methyl, ethyl, n-propyl, isopropyl, t-butyl, phenyl, 4-tolyl, 3,5-dimethylphenyl, 3,5-di(tert-butyl)phenyl, p-tert-butylphenyl and 1-naphthyl, and examples of particularly preferred radicals R$^{3a}$ and R$^{3b}$ are hydrogen, methyl, ethyl, n-propyl, isopropyl, t-butyl, phenyl, 4-tolyl, 3,5-dimethylphenyl, 3,5-di(tert-butyl)phenyl, p-tert-butylphenyl and 1-naphthyl.

The radicals R$^{4'}$ and R$^8$ are identical or different and are as defined for R$^3$ or R$^4$, or R$^{4'}$ and R$^8$ or two radicals R$^8$ together form a saturated or unsaturated, preferably unsaturated, 5- to 7-membered ring system.

Z is a bridge of the type SiR$^{16}$R$^{17}$, CR$^{16}$R$^{17}$ or C$_2$H$_4$, where R$^{16}$ and R$^{17}$ are identical or different and are each methyl, ethyl or phenyl. Particular preference is given to Z being dimethylsilyl, diphenylsilyl or ethylidene.

In a particularly preferred embodiment of the novel organometallic transition metal compounds of the formula (Ia), the fragments of the molecule have the following meanings:
M$^1$X$_2$ is ZrCl$_2$, ZrMe$_2$ or Zr(OR$^5$)$_2$, where R$^5$ is a C$_6$–C$_{10}$-aryl radical or a C$_7$–C$_{14}$-alkylaryl radical, each preferably having from 1 to 4 carbon atoms in the alkyl radical and 6 carbon atoms in the aryl radical, and two radicals R$^5$ may be joined to one another,
R$^1$ is isopropyl, cyclohexyl, cyclopentyl, phenyl, furyl or thienyl
R$^2$ is methyl, ethyl, n-propyl or n-butyl,
R$^3$ is methyl, ethyl or phenyl,
R$^{3a}$ and R$^{3b}$ are hydrogen, methyl, ethyl or phenyl, R⁴ is phenyl, 2-tolyl, 4-tolyl, 3,5-dimethylphenyl, 1-naphthyl, p-tert-butylphenyl or 3,5-di-t-butylphenyl, R⁴' is hydrogen, phenyl, 2-tolyl, 4-tolyl, 3,5-dimethylphenyl, 1-naphthyl or p-tert-butylphenyl, or 3,5-di-t-butylphenyl, R⁸ is hydrogen or the R⁸ in the ortho position relative to R⁴' and R⁴' together form a butadienylene group, Z is Me₂Si, Ph₂Si or ethylidene.

In a particularly preferred embodiment of the novel organometallic transition metal compounds of the formula (Ib) or (Ic), the fragments of the molecule have the following meanings:

$M^1X_2$ is $ZrCl_2$, $ZrMe_2$ or $Zr(OR^5)_2$, where $R^5$ is a $C_6$–$C_{10}$-aryl radical or a $C_7$–$C_{14}$-alkylaryl radical, each preferably having from 1 to 4 carbon atoms in the alkyl radical and 6 carbon atoms in the aryl radical, and two radicals $R^5$ may be joined to one another, R¹ is isopropyl, cyclohexyl, cyclopentyl, phenyl, furyl or thienyl R² is methyl, ethyl, n-propyl or n-butyl, R³ is methyl, ethyl or phenyl.

$R^{3a}$ and $R^{3b}$ are hydrogen, methyl, ethyl or phenyl.

R⁴ is phenyl, 2-tolyl, 4-tolyl, 3,5-dimethylphenyl, 1-naphthyl, p-tert-butylphenyl or 3,5-di-t-butylphenyl, R⁴' is hydrogen, phenyl, 2-tolyl, 4-tolyl, 3,5-dimethylphenyl, 1-naphthyl or p-tert-butylphenyl, or 3,5-di-t-butylphenyl, R⁸ is hydrogen or the R⁸ in the ortho position relative to R⁴' and R⁴' together form a butadienylene group, Z is Me₂Si, Ph₂Si or ethylidene.

In comparison with the metallocenes known hitherto, the novel organometallic transition metal compounds of the formulae (I), (Ia), (Ib) and (Ic) give an increase in the previously achievable molar masses in the copolymerization of propylene with ethylene and at the same time give a sufficient molar mass and a high melting point of the isotactic polypropylene in the homopolymerization of propylene.

In the production of a catalyst, the organometallic transition metal compounds of the formulae (I), (Ia), (Ib) and (Ic) (rac or pseudo-rac) can, if appropriate, be used as a mixture together with the undesired diastereomers (meso or pseudo-meso) formed in their synthesis. The organometallic transition metal compounds of the formulae (I), (Ia), (Ib) and (Ic) give highly isotactic polypropylene while the corresponding undesired diastereomers generally give atactic polypropylene.

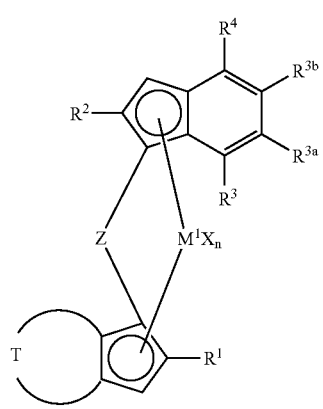

rac or psuedo-rac

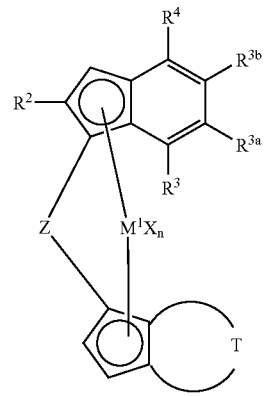

meso or psuedo-meso

Illustrative examples of novel organometallic transition metal compounds of the formula (I), which do not, however, restrict the scope of the invention, are:

dimethylsilanediyl(2,7-dimethyl-4-phenylindenyl)(2-isopropylindenyl)zirconium dichloride, dimethylsilanediyl(2,7-dimethyl-4-phenylindenyl)(2-isopropyl-4-methylindenyl) zirconium dichloride, dimethylsilanediyl(2,7-dimethyl-4-phenylindenyl)(2-isopropyl-5-methylindenyl)zirconium dichloride, dimethylsilanediyl(2,7-dimethyl-4-phenylindenyl)(2-isopropyl-6-methylindenyl)zirconium dichloride, dimethylsilanediyl(2,7-dimethyl-4-phenylindenyl)(2-isopropyl-7-methylindenyl)zirconium dichloride, dimethylsilanediyl(2,7-dimethyl-4-phenylindenyl)(2-isopropyl-4,7-dimethylindenyl)zirconium dichloride, dimethylsilanediyl (2,7-dimethyl-4-phenylindenyl)(2-isopropyl-5,6-dimethylindenyl)zirconium dichloride, dimethylsilanediyl (2,7-dimethyl-4-phenylindenyl)(2-isopropyl-4,5,6,7-tetramethylindenyl)zirconium dichloride, dimethylsilanediyl(2,7-dimethyl-4-phenylindenyl)(2,4-diisopropylindenyl)zirconium dichloride, dimethylsilanediyl (2,7-dimethyl-4-phenylindenyl)(2,4,6-triisopropylindenyl) zirconium dichloride, dimethylsilanediyl(2,7-dimethyl-4-phenylindenyl)(2,4-diisopropyl-7-methylindenyl)zirconium dichloride, dimethylsilanediyl(2,7-dimethyl-4-phenylindenyl)(2-isopropyl-4,5-benzindenyl)zirconium dichloride, dimethylsilanediyl(2,6-dimethyl-4-phenylindenyl)(2-isopropylindenyl)zirconium dichloride, dimethylsilanediyl(2,5-dimethyl-4-phenylindenyl)(2-isopropyl-4-methylindenyl) zirconium dichloride, dimethylsilanediyl(2,5,7-trimethyl-4-phenylindenyl)(2-isopropyl-5-methylindenyl)zirconium dichloride, dimethylsilanediyl(2,5,7-trimethyl-4-phenylindenyl)(2-isopropyl-6-methylindenyl)zirconium dichloride, dimethylsilanediyl(2,5,6-trimethyl-4-phenylindenyl)(2-isopropyl-7-methylindenyl)zirconium dichloride, dimethylsilanediyl(2,5,6,7-tetramethyl-4-phenylindenyl)(2-isopropyl-4,7-dimethylindenyl)zirconium dichloride, dimethylsilanediyl(2,7-dimethyl-4-phenylindenyl)(5-isopropyl-cyclopenta[2,3-b]thiophen-6-yl)zirconium dichloride, dimethylsilanediyl(2,7-dimethyl-4-phenylindenyl)(5-isopropyl-2,3-dimethylcyclopenta[2,3-b]thiophen-4-yl) zirconium dichloride, dimethylsilanediyl(2,7-dimethyl-4-phenylindenyl)(5-isopropyl-3-methylcyclopenta[2,3-b] thiophen-6-yl)zirconium dichloride, dimethylsilanediyl(2,7-dimethyl-4-phenylindenyl)(3,5-diisopropyl-cyclopenta[2,3-b]thiophen-6-yl)zirconium dichloride, dimethylsilanediyl(2,7-dimethyl-4-phenylindenyl)(5-isopropyl-1-methylcyclopenta[3,2-b]pyrrol-4-yl)zirconium dichloride, dimethylsilanediyl(2,7-dimethyl-4-phenylindenyl)(5-isopropyl-1,2,3-trimethylcyclopenta[3,2-b]pyrrol-4-yl)zirconium dichloride, dimethylsilanediyl(2,7-dimethyl-4-phenylindenyl)(1,5-diisopropyl-cyclopenta[3,2-b]pyrrol-4-yl)zirconium dichloride, dimethylsilanediyl(2,7-dimethyl-4-phenylindenyl)(2-isopropyl-4-phenylindenyl)zirconium dichloride, dimethylsilanediyl(2,7-dimethyl-4-phenylindenyl)(2-isopropyl-4-phenyl-7-methylindenyl)zirconium dichloride, dimethylsilanediyl(2,6-dimethyl-4-phenylindenyl)(2-isopropyl-4-phenylindenyl)zirconium dichloride, dimethylsilanediyl(2,7-dimethyl-4-(2-tolyl)indenyl)(2-isopropyl-4-(2-tolyl)indenyl)zirconium dichloride, dimethylsilanediyl(2,7-dimethyl-4-(3-tolyl)indenyl)(2-isopropyl-4-(3-tolyl)indenyl)zirconium dichloride, dimethylsilanediyl(2,7-dimethyl-4-(4-tolyl)indenyl)(2-isopropyl-4-(4-tolyl)indenyl)zirconium dichloride, dimethylsilanediyl(2,7-dimethyl-4-(2,3-dimethylphenyl)indenyl)(2-isopropyl-4-(2,3-dimethylphenyl)indenyl)zirconium dichloride, dimethylsilanediyl(2,7-dimethyl-4-(2,4-dimethylphenyl)indenyl)(2-isopropyl-4-(2,4-dimethylphenyl)indenyl)zirconium dichloride, dimethylsilanediyl(2,7-dimethyl-4-(2,5-dimethylphenyl)indenyl)(2-isopropyl-4-(2,5-dimethylphenyl)indenyl)zirconium dichloride, dimethylsilanediyl(2,7-dimethyl-4-(2,6-dimethylphenyl)indenyl)(2-isopropyl-4-(2,6-dimethylphenyl)indenyl)zirconium dichloride, dimethylsilanediyl(2,7-dimethyl-4-(3,4-dimethylphenyl)indenyl)(2-isopropyl-4-(3,4-dimethylphenyl)indenyl)zirconium dichloride, dimethylsilanediyl(2,7-dimethyl-4-(3,5-dimethylphenyl)indenyl)(2-isopropyl-4-(3,5-dimethylphenyl)indenyl)zirconium dichloride, dimethylsilanediyl(2,7-dimethyl-4-(2,4,6-trimethylphenyl)indenyl)(2-isopropyl-4-(2,4,6-trimethylphenyl)indenyl)zirconium dichloride, dimethylsilanediyl(2,7-dimethyl-4-(2,3,4-trimethylphenyl)indenyl)(2-isopropyl-4-(2,3,4-trimethylphenyl)indenyl)zirconium dichloride, dimethylsilanediyl(2,7-dimethyl-4-(1-naphthyl)indenyl)(2-isopropyl-4-(1-naphthyl)indenyl)zirconium dichloride, dimethylsilanediyl(2,7-dimethyl-4-(2-naphthyl)indenyl)(2-isopropyl-4-(2-naphthyl)indenyl)zirconium dichloride, dimethylsilanediyl(2,7-dimethyl-4-phenanthrenylindenyl)(2-isopropyl-4-phenanthrenylindenyl)zirconium dichloride, dimethylsilanediyl(2,7-dimethyl-4-(p-isopropylphenyl)indenyl)(2-isopropyl-4-(p-isopropylphenyl)indenyl)zirconium dichloride, dimethylsilanediyl(2,7-dimethyl-4-(p-tert-butylphenyl)indenyl)(2-isopropyl-4-(p-tert-butylphenyl)indenyl)zirconium dichloride, dimethylsilanediyl(2,7-dimethyl-4-(p-cyclohexylphenyl)indenyl)(2-isopropyl-4-(p-cyclohexylphenyl)indenyl)zirconium dichloride, dimethylsilanediyl(2,7-dimethyl-4-(p-trimethylsilylphenyl)indenyl)(2-isopropyl-4-(p-trimethylsilylphenyl)indenyl)zirconium dichloride, dimethylsilanediyl(2-methyl-4,6-bis-phenylindenyl)(2-isopropyl-4-phenylindenyl)zirconium dichloride, dimethylsilanediyl(2-methyl-4,7-bis-phenylindenyl)(2-isopropyl-4-phenylindenyl)zirconium dichloride, dimethylsilanediyl(2-methyl-4,6-bis(4-tolyl)indenyl)(2-isopropyl-4-(4-tolyl)indenyl)zirconium dichloride, dimethylsilanediyl(2-methyl-4,6-bis(3,5-dimethylphenyl)indenyl)(2-isopropyl-4-(3,5-dimethylphenyl)indenyl)zirconium dichloride, dimethylsilanediyl(2-methyl-4,6-bis(1-naphthyl)indenyl)(2-isopropyl-4-(1-naphthyl)indenyl)zirconium dichloride, dimethylsilanediyl(2-methyl-4,6-bis(p-tert-butylphenyl)indenyl)(2-isopropyl-4-(p-tert-butylphenyl)indenyl)zirconium dichloride, dimethylsilanediyl(2,7-dimethyl-4-(2-tolyl)indenyl)(2-isopropyl-4-phenylindenyl)zirconium dichloride, dimethylsilanediyl(2,7-dimethyl-4-(3-tolyl)indenyl)(2-isopropyl-4-phenylindenyl)zirconium dichloride, dimethylsilanediyl(2,7-dimethyl-4-(2,3-dimethylphenyl)indenyl)(2-isopropyl-4-phenylindenyl)zirconium dichloride, dimethylsilanediyl(2,7-dimethyl-4-(2,4-dimethylphenyl)indenyl)(2-isopropyl-4-phenylindenyl)zirconium dichloride, dimethylsilanediyl(2,7-dimethyl-4-(2,5-dimethylphenyl)indenyl)(2-isopropyl-4-phenylindenyl)zirconium dichloride, dimethylsilanediyl(2,7-dimethyl-4-(2,6-dimethylphenyl)indenyl)(2-isopropyl-4-phenylindenyl)zirconium dichloride, dimethylsilanediyl(2,7-dimethyl-4-(3,4-dimethylphenyl)indenyl)(2-isopropyl-4-phenylindenyl)zirconium dichloride, dimethylsilanediyl(2,7-dimethyl-4-(3,5-dimethylphenyl)indenyl)(2-isopropyl-4-phenylindenyl)zirconium dichloride, dimethylsilanediyl(2,7-dimethyl-4-(2,4,6-trimethylphenyl)indenyl)(2-isopropyl-4-phenylindenyl)zirconium dichloride, dimethylsilanediyl(2,7-dimethyl-4-(2,3,4-trimethylphenyl)indenyl)(2-isopropyl-4-phenylindenyl)zirconium dichloride, dimethylsilanediyl(2,7-dimethyl-4-(1-naphthyl)indenyl)(2-isopropyl-4-phenylindenyl)zirconium dichloride, dimethylsilanediyl(2,7-dimethyl-4-(2-naphthyl)indenyl)(2-isopropyl-4-phenylindenyl)zirconium dichloride, dimethylsilanediyl(2,7-dimethyl-4-phenanthrenylindenyl)(2-isopropyl-4-phenylindenyl)zirconium dichloride, dimethylsilanediyl(2,7-dimethyl-4-(p-isopropylphenyl)indenyl)(2-isopropyl-4-phenylindenyl)zirconium dichloride, dimethylsilanediyl(2,7-dimethyl-4-(p-tert-butylphenyl)indenyl)(2-isopropyl-4-phenylindenyl)zirconium dichloride, dimethylsilanediyl(2,7-dimethyl-(3,5-di-(p-tert-butyl)phenyl)indenyl)(2-isopropyl-4-phenylindenyl)zirconium dichloride, dimethylsilanediyl(2,7-dimethyl-4-(p-cyclohexylphenyl)indenyl)(2-isopropyl-4-phenylindenyl)zirconium dichloride, dimethylsilanediyl(2,7-dimethyl-4-(p-trimethylsilylphenyl)indenyl)(2-isopropyl-4-phenylindenyl)zirconium dichloride, dimethylsilanediyl(2-methyl-4,6-di-phenylindenyl)(2-isopropyl-4-phenylindenyl)zirconium dichloride, dimethylsilanediyl(2-methyl-4,6-bis(3,5-dimethylphenyl)indenyl)(2-isopropyl-4-phenylindenyl)zirconium dichloride, dimethylsilanediyl(2-methyl-4,6-bis(1-naphthyl)indenyl)(2-isopropyl-4-phenylindenyl)zirconium dichloride, dimethylsilanediyl(2-methyl-4,6-bis(p-tert-butylphenyl)indenyl)(2-isopropyl-4-phenylindenyl)zirconium dichloride, dimethylsilanediyl(2-methyl-(3,5-di-(p-tert-butyl)phenyl)indenyl)(2-isopropyl-4-phenylindenyl)zirconium dichloride, dimethylsilanediyl(2,7-dimethyl-4-phenylindenyl)(2-isopropyl-4-(2-tolyl)indenyl)zirconium dichloride, dimethylsilanediyl(2,7-dimethyl-4-phenylindenyl)(2-isopropyl-4-(3-tolyl)indenyl)zirconium dichloride, dimethylsilanediyl(2,7-dimethyl-4-phenylindenyl)(2-isopropyl-4-(4-tolyl)indenyl)zirconium dichloride, dimethylsilanediyl(2,7-dimethyl-4-phenylindenyl)(2-isopropyl-4-(2,3-dimethylphenyl)indenyl)zirconium dichloride, dimethylsilanediyl(2,7-dimethyl-4-phenylindenyl)(2-isopropyl-4-(2,4-dimethylphenyl)indenyl)zirconium dichloride, dimethylsilanediyl(2,7-dimethyl-4-phenylindenyl)(2-isopropyl-4-(2,5-dimethylphenyl)indenyl)zirconium dichloride, dimethylsilanediyl(2,7-dimethyl-4-phenylindenyl)(2-isopropyl-4-(2,6-dimethylphenyl)indenyl)zirconium dichloride, dimethylsilanediyl(2,7-dimethyl-4-phenylindenyl)(2-isopropyl-4-(3,4-dimethylphenyl)indenyl)zirconium dichloride, dimethylsilanediyl(2,7-dimethyl-4-phenylindenyl)(2-isopropyl-4-(3,5-dimethylphenyl)indenyl)zirconium dichloride, dimethylsilanediyl(2,7-dimethyl-4-phenylindenyl)(2-isopropyl-4-(2,4,6-trimethylphenyl)indenyl)zirconium dichloride, dimethylsilanediyl(2,7-dimethyl-4-phenylindenyl)(2-isopropyl-4-(2,3,4-trimethylphenyl)indenyl) zirconium dichloride, dimethylsilanediyl(2,7-dimethyl-4-phenylindenyl)(2-isopropyl-4-(1-naphthyl)indenyl) zirconium dichloride, dimethylsilanediyl(2,7-dimethyl-4-phenylindenyl)(2-isopropyl-4-(2-naphthyl)indenyl) zirconium dichloride, dimethylsilanediyl(2,7-dimethyl-4-phenylindenyl)(2-isopropyl-4-phenanthrenylindenyl) zirconium dichloride, dimethylsilanediyl(2,7-dimethyl-4-phenylindenyl)(2-isopropyl-4-(p-isopropylphenyl)indenyl) zirconium dichloride, dimethylsilanediyl(2,7-dimethyl-4-phenylindenyl)(2-isopropyl-4-(p-tert-butylphenyl)indenyl) zirconium dichloride, dimethylsilanediyl(2,7-dimethyl-4-phenylindenyl)(2-isopropyl-4-(p-cyclohexylphenyl) indenyl)zirconium dichloride, dimethylsilanediyl(2,7-dimethyl-4-phenylindenyl)(2-isopropyl-4-(p-trimethylsilylphenyl)indenyl)zirconium dichloride, dimethylsilanediyl(2-methyl-4,6-diphenylindenyl)(2-isopropyl-4-(4-tolyl)indenyl)zirconium dichloride, dimethylsilanediyl(2-methyl-4,6-diphenylindenyl)(2-isopropyl-4-(3,5-dimethylphenyl)indenyl)zirconium dichloride, dimethylsilanediyl(2-methyl-4,6-diphenylindenyl)(2-isopropyl-4-(1-naphthyl)indenyl)zirconium dichloride, dimethylsilanediyl(2-methyl-4,6-diphenylindenyl)(2-isopropyl-4-(p-tert-butylphenyl)indenyl)zirconium dichloride, dimethylsilanediyl(2,7-dimethyl-4-(2-tolyl)indenyl)(2-isopropyl-4-(1-naphthyl)indenyl)zirconium dichloride, dimethylsilanediyl(2,7-dimethyl-4-(3-tolyl)indenyl)(2-isopropyl-4-(1-naphthyl)indenyl)zirconium dichloride, dimethylsilanediyl(2,7-dimethyl-4-(4-tolyl)indenyl)(2-isopropyl-4-(1-naphthyl)indenyl)zirconium dichloride, dimethylsilanediyl(2,7-dimethyl-4-(2,3-dimethylphenyl)indenyl) (2-isopropyl-4-(1-naphthyl)indenyl)zirconium dichloride, dimethylsilanediyl(2,7-dimethyl-4-(2,4-dimethylphenyl) indenyl)(2-isopropyl-4-(1-naphthyl)indenyl)zirconium dichloride, dimethylsilanediyl(2,7-dimethyl-4-(2,5-dimethylphenyl)indenyl)(2-isopropyl-4-(1-naphthyl)indenyl)zirconium dichloride, dimethylsilanediyl(2,7-dimethyl-4-(2,6-dimethylphenyl)indenyl)(2-isopropyl-4-(naphthyl)indenyl) zirconium dichloride, dimethylsilanediyl(2,7-dimethyl-4-(3,4-dimethylphenyl)indenyl)(2-isopropyl-4-(1-naphthyl) indenyl)zirconium dichloride, dimethylsilanediyl(2,7-dimethyl-4-(3,5-dimethylphenyl)indenyl)(2-isopropyl-4-(1-naphthyl)indenyl)zirconium dichloride, dimethylsilanediyl (2,7-dimethyl-4-(2,4,6-trimethylphenyl)indenyl)(2-isopropyl-4-(1-naphthyl)indenyl)zirconium dichloride, dimethylsilanediyl(2,7-dimethyl-4-(2,3,4-trimethylphenyl) indenyl)(2-isopropyl-4-(1-naphthyl)indenyl)zirconium dichloride, dimethylsilanediyl(2,7-dimethyl-4-(2-naphthyl) indenyl)(2-isopropyl-4-(1-naphthyl)indenyl)zirconium dichloride, dimethylsilanediyl(2,7-dimethyl-4-phenanthrenylindenyl)(2-isopropyl-4-(1-naphthyl)indenyl)zirconium dichloride, dimethylsilanediyl(2,7-dimethyl-4-(p-isopropylphenyl)indenyl)(2-isopropyl-4-(1-naphthyl)indenyl)zirconium dichloride, dimethylsilanediyl(2,7-dimethyl-4-(p-tert-butylphenyl)indenyl)(2-isopropyl-4-(naphthyl)indenyl) zirconium dichloride, dimethylsilanediyl(2,7-dimethyl-4-(3,5-di(p-tert-butyl)phenyl)indenyl)(2-isopropyl-4-(1-naphthyl) indenyl)zirconium dichloride, dimethylsilanediyl(2,7-dimethyl-4-(p-cyclohexylphenyl)indenyl)(2-isopropyl-4-(1-naphthyl)indenyl)zirconium dichloride, dimethylsilanediyl (2,7-dimethyl-4-(p-trimethylsilylphenyl)indenyl)(2-isopropyl-4-(1-naphthyl)indenyl)zirconium dichloride, dimethylsilanediyl(2-methyl-4,6-bis(4-tolyl)indenyl)(2-isopropyl-4-(1-naphthyl)indenyl)zirconium dichloride, dimethylsilanediyl(2-methyl-4,6-bis(3,5-dimethylphenyl)indenyl)(2-isopropyl-4-(1-naphthyl)indenyl)zirconium dichloride, dimethylsilanediyl(2-methyl-4,6-bis(1-naphthyl) indenyl)(2-isopropyl-4-(1-naphthyl)indenyl)zirconium dichloride, dimethylsilanediyl(2-methyl-4,6-bis(p-tert-butylphenyl)indenyl)(2-isopropyl-4-(naphthyl)indenyl)zirconium dichloride, dimethylsilanediyl(2,7-dimethyl-4-(1-naphthyl)indenyl) (2-isopropyl-4-(2-tolyl)indenyl)zirconium dichloride, dimethylsilanediyl(2,7-dimethyl-4-(1-naphthyl)indenyl)(2-isopropyl-4-(3-tolyl)indenyl)zirconium dichloride, dimethylsilanediyl(2,7-dimethyl-4-(1-naphthyl)indenyl)(2-isopropyl-4-(4-tolyl)indenyl)zirconium dichloride, dimethylsilanediyl(2,7-dimethyl-4-(1-naphthyl)indenyl)(2-isopropyl-4-(2,3-dimethylphenyl)indenyl)zirconium dichloride, dimethylsilanediyl(2,7-dimethyl-4-(1-naphthyl)indenyl)(2-isopropyl-4-(2,4-dimethylphenyl)indenyl)zirconium dichloride, dimethylsilanediyl(2,7-dimethyl-4-(naphthyl)indenyl) (2-isopropyl-4-(2,5-dimethylphenyl)indenyl)zirconium dichloride, dimethylsilanediyl(2,7-dimethyl-4-(1-naphthyl) indenyl)(2-isopropyl-4-(2,6-dimethylphenyl)indenyl)zirconium dichloride, dimethylsilanediyl(2,7-dimethyl-4-(1-naphthyl)indenyl)(2-isopropyl-4-(3,4-dimethylphenyl) indenyl)zirconium dichloride, dimethylsilanediyl(2,7-dimethyl-4-(1-naphthyl)indenyl)(2-isopropyl-4-(3,5-dimethylphenyl)indenyl)zirconium dichloride, dimethylsilanediyl(2,7-dimethyl-4-(1-naphthyl)indenyl)(2-isopropyl-4-(2,4,6-trimethylphenyl)indenyl)zirconium dichloride, dimethylsilanediyl(2,7-dimethyl-4-(1-naphthyl) indenyl)(2-isopropyl-4-(2,3,4-trimethylphenyl)indenyl)zirconium dichloride, dimethylsilanediyl(2,7-dimethyl-4-(1-naphthyl)indenyl)(2-isopropyl-4-(2-naphthyl)indenyl) zirconium dichloride, dimethylsilanediyl(2,7-dimethyl-4-(1-naphthyl)indenyl)(2-isopropyl-4-phenanthrenylindenyl) zirconium dichloride, dimethylsilanediyl(2-methyl-4,6-bis(1-naphthyl)indenyl) (2-isopropyl-4-(4-tolyl)indenyl)zirconium dichloride, dimethylsilanediyl(2-methyl-4,6-bis(1-naphthyl)indenyl)(2-isopropyl-4-(3,5-dimethylphenyl)indenyl)zirconium dichloride, dimethylsilanediyl(2-methyl-4,6-bis(1-naphthyl) indenyl)indenyl)(2-isopropyl-4-(p-tert-butylphenyl)indenyl)zirconium dichloride, dimethylsilanediyl(2,7-dimethyl-4-(2-tolyl)indenyl)(2-isopropyl-4-(p-t-butylphenyl)indenyl)zirconium dichloride, dimethylsilanediyl(2,7-dimethyl-4-(3-tolyl)indenyl)(2-isopropyl-4-(p-t-butylphenyl)indenyl)zirconium dichloride, dimethylsilanediyl(2,7-dimethyl-4-(4-tolyl)indenyl)(2-isopropyl-4-(p-t-butylphenyl)indenyl)zirconium dichloride, dimethylsilanediyl(2,7-dimethyl-4-(2,3-dimethylphenyl)indenyl)(2-isopropyl-4-(p-t-butylphenyl)indenyl)zirconium dichloride, dimethylsilanediyl(2,7-dimethyl-4-(2,4-dimethylphenyl)indenyl)(2-isopropyl-4-(p-t-butylphenyl)indenyl) zirconium dichloride, dimethylsilanediyl(2,7-dimethyl-4-(2,5-dimethylphenyl)indenyl)(2-isopropyl-4-(p-t-butylphenyl) indenyl)zirconium dichloride, dimethylsilanediyl(2,7-dimethyl-4-(2,6-dimethylphenyl)indenyl)(2-isopropyl-4-(p-t-butylphenyl)indenyl)zirconium dichloride, dimethylsilanediyl(2,7-dimethyl-4-(3,4-dimethylphenyl)indenyl)(2-isopropyl-4-(p-t-butylphenyl)indenyl)zirconium dichloride, dimethylsilanediyl(2,7-dimethyl-4-(3,5-dimethylphenyl)indenyl)(2-isopropyl-4-(p-t-butylphenyl)indenyl) zirconium dichloride, dimethylsilanediyl(2,7-dimethyl-4-(2,4,6-trimethylphenyl)indenyl)(2-isopropyl-4-(p-t-butylphenyl)indenyl)zirconium dichloride, dimethylsilanediyl(2,7-dimethyl-4-(2,3,4-trimethylphenyl) indenyl)(2-isopropyl-4-(p-t-butylphenyl)indenyl)zirconium dichloride, dimethylsilanediyl(2,7-dimethyl-4-(1-naphthyl) indenyl)(2-isopropyl-4-(p-t-butylphenyl)indenyl)zirconium dichloride, dimethylsilanediyl(2,7-dimethyl-4-(2-naphthyl) indenyl)(2-isopropyl-4-(p-t-butylphenyl)indenyl)zirconium dichloride, dimethylsilanediyl(2,7-dimethyl-4-phenanthrenylindenyl)(2-isopropyl-4-(p-t-butylphenyl)indenyl)zirconium dichloride, dimethylsilanediyl(2,7-dimethyl-4-(p-isopropylphenyl)indenyl)(2-isopropyl-4-(p-t-butylphenyl)indenyl)zirconium dichloride, dimethylsilanediyl(2,7-dimethyl-4-(p-tert-butylphenyl)indenyl)(2-isopropyl-4-(p-t-butylphenyl)indenyl)zirconium dichloride, dimethylsilanediyl(2,7-dimethyl-(3,5-di(p-tert-butyl)phenyl)indenyl)(2-isopropyl-4-(p-t-butylphenyl)indenyl)zirconium dichloride, dimethylsilanediyl(2,7-dimethyl-4-(p-cyclohexylphenyl)indenyl)(2-isopropyl-4-(p-t-butylphenyl)indenyl)zirconium dichloride, dimethylsilanediyl(2,7-dimethyl-4-(p-trimethylsilylphenyl)indenyl)(2-isopropyl-4-(p-t-butylphenyl)indenyl)zirconium dichloride, dimethylsilanediyl(2-methyl-4,6-bis(4-tolyl)indenyl)(2-isopropyl-4-(p-t-butylphenyl)indenyl)zirconium dichloride, dimethylsilanediyl(2-methyl-4,6-bis(3,5-dimethylphenyl)indenyl)(2-isopropyl-4-(p-t-butylphenyl)indenyl)zirconium dichloride, dimethylsilanediyl(2-methyl-4,6-bis(1-naphthyl)indenyl)(2-isopropyl-4-(p-t-butylphenyl)indenyl)zirconium dichloride, dimethylsilanediyl(2-methyl-4,6-bis(p-tert-butylphenyl)indenyl)(2-isopropyl-4-(p-t-butylphenyl)indenyl)zirconium dichloride, dimethylsilanediyl(2-methyl-4,6-bis(3,5-di-(p-tert-butyl)-phenyl)indenyl)(2-isopropyl-4-(p-t-butylphenyl)indenyl)zirconium dichloride, dimethylsilanediyl(2,7-dimethyl-4-(p-t-butylphenyl)indenyl)(2-isopropyl-4-(2-tolyl)indenyl)zirconium dichloride, dimethylsilanediyl(2,7-dimethyl-4-(p-t-butylphenyl)indenyl)(2-isopropyl-4-(3-tolyl)indenyl)zirconium dichloride, dimethylsilanediyl(2,7-dimethyl-4-(p-t-butylphenyl)indenyl)(2-isopropyl-4-(4-tolyl)indenyl)zirconium dichloride, dimethylsilanediyl(2,7-dimethyl-4-(p-t-butylphenyl)indenyl)(2-isopropyl-4-(2,3-dimethylphenyl)indenyl)zirconium dichloride, dimethylsilanediyl(2,7-dimethyl-4-(p-t-butylphenyl)indenyl)(2-isopropyl-4-(2,4-dimethylphenyl)indenyl)zirconium dichloride, dimethylsilanediyl(2,7-dimethyl-4-(p-t-butylphenyl)indenyl)(2-isopropyl-4-(2,5-dimethylphenyl)indenyl)zirconium dichloride, dimethylsilanediyl(2,7-dimethyl-4-(p-t-butylphenyl)indenyl)(2-isopropyl-4-(2,6-dimethylphenyl)indenyl)zirconium dichloride, dimethylsilanediyl(2,7-dimethyl-4-(p-t-butylphenyl)indenyl)(2-isopropyl-4-(3,4-dimethylphenyl)indenyl)zirconium dichloride, dimethylsilanediyl(2,7-dimethyl-4-(p-t-butylphenyl)indenyl)(2-isopropyl-4-(3,5-dimethylphenyl)indenyl)zirconium dichloride, dimethylsilanediyl(2,7-dimethyl-4-(p-t-butylphenyl)indenyl)(2-isopropyl-4-(2,4,6-trimethylphenyl)indenyl)zirconium dichloride, dimethylsilanediyl(2,7-dimethyl-4-(p-t-butylphenyl)indenyl)(2-isopropyl-4-(2,3,4-trimethylphenyl)indenyl)zirconium dichloride, dimethylsilanediyl(2,7-dimethyl-4-(p-t-butylphenyl)indenyl)(2-isopropyl-4-(2-naphthyl)indenyl)zirconium dichloride, dimethylsilanediyl(2,7-dimethyl-4-(p-t-butylphenyl)indenyl)(2-isopropyl-4-phenanthrenylindenyl)zirconium dichloride, dimethylsilanediyl(2,7-dimethyl-4-(p-t-butylphenyl)indenyl)(2-isopropyl-4-(p-isopropylphenyl)indenyl)zirconium dichloride, dimethylsilanediyl(2,7-dimethyl-4-(p-t-butylphenyl)indenyl)(2-isopropyl-4-(p-tert-butylphenyl)indenyl)zirconium dichloride, dimethylsilanediyl(2,7-dimethyl-4-(p-t-butylphenyl)indenyl)(2-isopropyl-4-(p-sec-butylphenyl)indenyl)zirconium dichloride, dimethylsilanediyl(2,7-dimethyl-4-(p-t-butylphenyl)indenyl)(2-isopropyl-4-(p-cyclohexylphenyl)indenyl)zirconium dichloride, dimethylsilanediyl(2,7-dimethyl-4-(p-t-butylphenyl)indenyl)(2-isopropyl-4-(p-trimethylsilylphenyl)indenyl)zirconium dichloride, dimethylsilanediyl(2-methyl-4,6-bis(p-t-butylphenyl)indenyl)(2-isopropyl-4-(2,3-dimethylphenyl)indenyl)zirconium dichloride, dimethylsilanediyl(2-methyl-4,6-bis(p-t-butylphenyl)(2-isopropyl-4-(3,5-dimethylphenyl)indenyl)zirconium dichloride, dimethylsilanediyl(2-methyl-4,6-bis(p-t-butylphenyl)(2-isopropyl-4-(p-tert-butylphenyl)indenyl)zirconium dichloride, dimethylsilanediyl(2,7-dimethyl-4-phenylindenyl)(5-isopropyl-3-phenyl-2-methylcyclopenta[2,3-b]thiophen-6-yl)zirconium dichloride, dimethylsilanediyl(2,7-dimethyl-4-(1-naphthyl)indenyl)(5-isopropyl-3-(1-naphthyl)-2-methylcyclopenta[2,3-b]thiophen-6-yl)zirconium dichloride, dimethylsilanediyl(2,7-dimethyl-4-(p-t-butylphenyl)indenyl)(5-isopropyl-3-(p-t-butylphenyl)-2-methylcyclopenta[2,3-b]thiophen-6-yl)zirconium dichloride, dimethylsilanediyl(2,7-dimethyl-4-phenylindenyl)(5-isopropyl-3-(1-naphthyl)-2-methylcyclopenta[2,3-b]thiophen-6-yl)zirconium dichloride, dimethylsilanediyl(2,7-dimethyl-4-phenylindenyl)(5-isopropyl-3-(p-t-butylphenyl)-2-methylcyclopenta[2,3-b]thiophen-6-yl)zirconium dichloride, dimethylsilanediyl(2,7-dimethyl-4-(1-naphthyl)indenyl)(5-isopropyl-3-phenyl-2-methylcyclopenta[2,3-b]thiophen-6-yl)zirconium dichloride, dimethylsilanediyl(2,7-dimethyl-4-(p-t-butylphenyl)indenyl)(5-isopropyl-3-phenyl-2-methylcyclopenta[2,3-b]thiophen-6-yl)zirconium dichloride, dimethylsilanediyl(2,7-dimethyl-4-(1-naphthyl)indenyl)(5-isopropyl-3-(p-t-butylphenyl)-2-methylcyclopenta[2,3-b]thiophen-6-yl)zirconium dichloride, dimethylsilanediyl(2,7-dimethyl-4-(p-t-butylphenyl)indenyl)(5-isopropyl-3-(1-naphthyl)-2-methylcyclopenta[2,3-b]thiophen-6-yl)zirconium dichloride, dimethylsilanediyl(2,7-dimethyl-4-phenylindenyl)(5-isopropyl-1-phenyl-2-methyl-cyclopenta[3,2-b]pyrrol-4-yl)zirconium dichloride, dimethylsilanediyl(2,7-dimethyl-4-(1-naphthyl)indenyl)(5-isopropyl-1-(1-naphthyl)-2-methylcyclopenta[3,2-b]pyrrol-4-yl)zirconium dichloride, dimethylsilanediyl(2,7-dimethyl-4-(p-t-butylphenyl)indenyl)(5-isopropyl-1-(p-t-butylphenyl)-2-methylcyclopenta[3,2-b]pyrrol-4-yl)zirconium dichloride, dimethylsilanediyl(2,7-dimethyl-4-phenylindenyl)(5-isopropyl-1-(1-naphthyl)-2-methylcyclopenta[3,2-b]pyrrol-4-yl)zirconium dichloride, dimethylsilanediyl(2,7-dimethyl-4-phenylindenyl)(5-isopropyl-1-(p-t-butylphenyl)-2-methylcyclopenta[3,2-b]pyrrol-4-yl)zirconium dichloride, dimethylsilanediyl(2,7-dimethyl-4-(1-naphthyl)indenyl)(5-isopropyl-1-phenyl-2-methylcyclopenta[3,2-b]pyrrol-4-yl)zirconium dichloride, dimethylsilanediyl(2,7-dimethyl-4-(p-t-butylphenyl)indenyl)(5-isopropyl-1-phenyl-2-methylcyclopenta[3,2-b]pyrrol-4-yl)zirconium dichloride, dimethylsilanediyl(2,7-dimethyl-4-(1-naphthyl)indenyl)(5-isopropyl-1-(p-t-butylphenyl)-2-methylcyclopenta[3,2-b]pyrrol-4-yl)zirconium dichloride, dimethylsilanediyl(2,7-dimethyl-4-(p-t-butylphenyl)indenyl)(5-isopropyl-1-(1-naphthyl)-2-methylcyclopenta[3,2-b]pyrrol-4-yl)zirconium dichloride, dimethylsilanediyl(2-methyl-4,6-bis-phenylindenyl)(5-isopropyl-3-phenyl-2-methylcyclopenta[2,3-b]thiophen-6-yl)zirconium dichloride, dimethylsilanediyl(2-methyl-4,6-bis(1-naphthyl)indenyl)(5-isopropyl-3-(1-naphthyl)-2-methylcyclopenta[2,3-b]thiophen-6-yl)zirconium dichloride, dimethylsilanediyl(2-methyl-4,6-bis(p-t-butylphenyl)indenyl)(5-isopropyl-3-(p-t-butylphenyl)-2-methylcyclopenta[2,3-b]thiophen-6-yl)zirconium dichloride, dimethylsilanediyl(2-methyl-4,6-bisphenylindenyl)(5-isopropyl-3-(1-naphthyl)-2-methylcyclopenta[2,3-b]thiophen-6-yl)zirconium dichloride, dimethylsilanediyl(2-methyl-4,6-bisphenylindenyl)(5-isopropyl-3-(p-t-butylphenyl)-2-methylcyclopenta[2,3-b]thiophen-6-yl)zirconium dichloride, dimethylsilanediyl(2-methyl-4,6-bis(1-naphthyl)indenyl)(5-isopropyl-3-phenyl-2-methylcyclopenta[2,3-b]thiophen-6-yl)zirconium dichloride, dimethylsilanediyl(2-methyl-4,6-bis(p-t-butylphenyl)indenyl)(5-isopropyl-3-phenyl-2-methylcyclopenta[2,3-b]thiophen-6-yl)zirconium dichloride, dimethylsilanediyl(2-methyl-4,6-bis(1-naphthyl)indenyl)(5-isopropyl-3-(p-t-butylphenyl)-2-methylcyclopenta[2,3-b]thiophen-6-yl)zirconium dichloride, dimethylsilanediyl(2-methyl-4,6-bis(p-t-butylphenyl)indenyl)(5-isopropyl-3-(1-naphthyl)-2-methylcyclopenta[2,3-b]thiophen-6-yl)zirconium dichloride, dimethylsilanediyl(2-methyl-4,6-bisphenylindenyl)(5-isopropyl-1-phenyl-2-methylcyclopenta[3,2-b]pyrrol-4-yl)zirconium dichloride, dimethylsilanediyl(2-methyl-4,6-bis(1-naphthyl)indenyl)(5-isopropyl-1-(1-naphthyl)-2-methylcyclopenta[3,2-b]pyrrol-4-yl)zirconium dichloride, dimethylsilanediyl(2-methyl-4,6-bis(p-t-butylphenyl)indenyl)(5-isopropyl-1-(p-t-butylphenyl)-2-methylcyclopenta[3,2-b]pyrrol-4-yl)zirconium dichloride, dimethylsilanediyl(2-methyl-4,6-bis-phenylindenyl)(5-isopropyl-1-(1-naphthyl)-2-methylcyclopenta[3,2-b]pyrrol-4-yl)zirconium dichloride, dimethylsilanediyl(2-methyl-4,6-bis-phenylindenyl)(5-isopropyl-1-(p-t-butylphenyl)-2-methylcyclopenta[3,2-b]pyrrol-4-yl)zirconium dichloride, dimethylsilanediyl(2-methyl-4,6-bis(1-naphthyl)indenyl)(5-isopropyl-1-phenyl-2-methylcyclopenta[3,2-b]pyrrol-4-yl)zirconium dichloride, dimethylsilanediyl(2-methyl-4,6-bis(p-t-butylphenyl)indenyl)(5-isopropyl-1-phenyl-2-methylcyclopenta[3,2-b]pyrrol-4-yl)zirconium dichloride, dimethylsilanediyl(2-methyl-4,6-bis(1-naphthyl)indenyl)(5-isopropyl-1-(p-t-butylphenyl)-2-methylcyclopenta[3,2-b]pyrrol-4-yl)zirconium dichloride, dimethylsilanediyl(2-methyl-4,6-bis(p-t-butylphenyl)indenyl)(5-isopropyl-1-(1-naphthyl)-2-methylcyclopenta[3,2-b]pyrrol-4-yl)zirconium dichloride, dimethylsilanediyl(2,7-dimethyl-4-phenylindenyl)(2-(1-methylpropyl)-4-phenylindenyl)zirconium dichloride, dimethylsilanediyl(2,7-dimethyl-4-phenylindenyl)(2-(1-methylbutyl)-4-phenylindenyl)zirconium dichloride, dimethylsilanediyl(2,7-dimethyl-4-phenylindenyl)(2-(1-ethylbutyl)-4-phenylindenyl)zirconium dichloride, dimethylsilanediyl(2,7-dimethyl-4-phenylindenyl)(2-(1-methylpentyl)-4-phenylindenyl)zirconium dichloride, dimethylsilanediyl(2,7-dimethyl-4-phenylindenyl)(2-cyclopentyl-4-phenylindenyl)zirconium dichloride, dimethylsilanediyl(2,7-dimethyl-4-phenylindenyl)(2-cyclohexyl-4-phenylindenyl)zirconium dichloride, dimethylsilanediyl(2,7-dimethyl-4-phenylindenyl)(2-t-butyl-4-phenylindenyl)zirconium dichloride, dimethylsilanediyl(2,7-dimethyl-4-phenylindenyl)(2-(cyclopent-2-enyl)-4-phenylindenyl)zirconium dichloride, dimethylsilanediyl(2,7-dimethyl-4-phenylindenyl)(2-(cyclopent-3-enyl)-4-phenylindenyl)zirconium dichloride, dimethylsilanediyl(2,7-dimethyl-4-phenylindenyl)(2-cyclohex-2-enyl)-4-phenylindenyl)zirconium dichloride, dimethylsilanediyl(2,7-dimethyl-4-phenylindenyl)(2-(cyclohex-3-enyl)-4-phenylindenyl)zirconium dichloride, dimethylsilanediyl(2,7-dimethyl-4-phenylindenyl)(2-diphenylmethyl-4-phenylindenyl)zirconium dichloride, dimethylsilanediyl(2,7-dimethyl-4-phenylindenyl)(2-triphenylethyl-4-phenylindenyl)zirconium dichloride, dimethylsilanediyl(2,7-dimethyl-4-phenylindenyl)(2-phenyl-4-phenylindenyl)zirconium dichloride, dimethylsilanediyl(2,7-dimethyl-4-phenylindenyl)(2-(2-tolyl)-4-phenylindenyl)zirconium dichloride, dimethylsilanediyl(2,7-dimethyl-4-phenylindenyl)(2-(3-tolyl)-4-phenylindenyl)zirconium dichloride, dimethylsilanediyl(2,7-dimethyl-4-phenylindenyl)(2-(4-tolyl)-4-phenylindenyl)zirconium dichloride, dimethylsilanediyl(2,7-dimethyl-4-phenylindenyl)(2-(2,6-dimethylphenyl)-4-phenylindenyl)zirconium dichloride, dimethylsilanediyl(2,7-dimethyl-4-phenylindenyl)(2-(2,4,6-trimethylphenyl)-4-phenylindenyl)zirconium dichloride, dimethylsilanediyl(2,7-dimethyl-4-phenylindenyl)(2-(1-naphthyl)-4-phenylindenyl)zirconium dichloride, dimethylsilanediyl(2,7-dimethyl-4-phenylindenyl)(2-(2-naphthyl)-4-phenylindenyl)zirconium dichloride, dimethylsilanediyl(2,7-dimethyl-4-phenylindenyl)(2-phenanthrenyl-4-phenylindenyl)zirconium dichloride, dimethylsilanediyl(2,7-dimethyl-4-phenylindenyl)(2-trimethylsilyl-4-phenylindenyl)zirconium dichloride, dimethylsilanediyl(2,7-dimethyl-4-(1-naphthyl)indenyl)(2-sec-butyl-4-(1-naphthyl)indenyl)zirconium dichloride, dimethylsilanediyl(2,7-dimethyl-4-(1-naphthyl)indenyl)(2-cyclobutyl-4-(1-naphthyl)indenyl)zirconium dichloride, dimethylsilanediyl(2,7-dimethyl-4-(1-naphthyl)indenyl)(2-(1-methylpropyl)-4-(1-naphthyl)indenyl)zirconium dichloride, dimethylsilanediyl(2,7-dimethyl-4-(1-naphthyl)indenyl)(2-(1-methylbutyl)-4-(1-naphthyl)indenyl)zirconium dichloride, dimethylsilanediyl(2,7-dimethyl-4-(1-naphthyl)indenyl)(2-(1-ethylbutyl)-4-(1-naphthyl)indenyl)zirconium dichloride, dimethylsilanediyl(2,7-dimethyl-4-(1-naphthyl)indenyl)(2-(1-methylpentyl)-4-(1-naphthyl)indenyl)zirconium dichloride, dimethylsilanediyl(2,7-dimethyl-4-(1-naphthyl)indenyl)(2-cyclopentyl-4-(1-naphthyl)indenyl)zirconium dichloride, dimethylsilanediyl(2,7-dimethyl-4-(1-naphthyl)indenyl)(2-cyclohexyl-4-(1-naphthyl)indenyl)zirconium dichloride, dimethylsilanediyl(2,7-dimethyl-4-(1-naphthyl)indenyl)(2-t-butyl-4-(1-naphthyl)indenyl)zirconium dichloride, dimethylsilanediyl(2,7-dimethyl-4-(1-naphthyl)indenyl)(2-(cyclopent-2-enyl)-4-(1-naphthyl)indenyl)zirconium dichloride, dimethylsilanediyl(2,7-dimethyl-4-(1-naphthyl)indenyl)(2-(cyclopent-3-enyl)-4-(1-naphthyl)indenyl)zirconium dichloride, dimethylsilanediyl(2,7-dimethyl-4-(1-naphthyl)indenyl)(2-cyclohex-2-enyl)-4-(1-naphthyl)indenyl)zirconium dichloride, dimethylsilanediyl(2,7-dimethyl-4-(1-naphthyl)indenyl)(2-(cyclohex-3-enyl)-4-(1-naphthyl)indenyl)zirconium dichloride, dimethylsilanediyl(2,7-dimethyl-4-(1-naphthyl)indenyl)(2-diphenylmethyl-4-(1-naphthyl)indenyl)zirconium dichloride, dimethylsilanediyl(2,7-dimethyl-4-(1-naphthyl)indenyl)(2-triphenylethyl-4-(1-naphthyl)indenyl)zirconium dichloride, dimethylsilanediyl(2,7-dimethyl-4-(1-naphthyl)indenyl)(2-phenyl-4-(1-naphthyl)indenyl)zirconium dichloride, dimethylsilanediyl(2,7-dimethyl-4-(1-naphthyl)indenyl)(2-(2-tolyl)-4-(1-naphthyl)indenyl)zirconium dichloride, dimethylsilanediyl(2,7-dimethyl-4-(1-naphthyl)indenyl)(2-(3-tolyl)-4-(1-naphthyl)indenyl)zirconium dichloride, dimethylsilanediyl(2,7-dimethyl-4-(1-naphthyl)indenyl)(2-(4-tolyl)-4-(1-naphthyl)indenyl)zirconium dichloride, dimethylsilanediyl(2,7-dimethyl-4-(1-naphthyl)indenyl)(2-(2,6-dimethylphenyl)-4-(1-naphthyl)indenyl)zirconium dichloride, dimethylsilanediyl(2,7-dimethyl-4-(1-naphthyl)indenyl)(2-(2,4,6-trimethylphenyl)-4-(1-naphthyl)indenyl)zirconium dichloride, dimethylsilanediyl(2,7-dimethyl-4-(1-naphthyl)indenyl)(2-(1-naphthyl)-4-phenylindenyl)zirconium dichloride, dimethylsilanediyl(2,7-dimethyl-4-(1-naphthyl)indenyl)(2-(2-naphthyl)-4-(1-naphthyl)indenyl)zirconium dichloride, dimethylsilanediyl(2,7-dimethyl-4-(1-naphthyl)indenyl)(2-phenanthrenyl-4-(1-naphthyl)indenyl)zirconium dichloride, dimethylsilanediyl(2,7-dimethyl-4-(1-naphthyl)indenyl)(2-trimethylsilyl-4-(1-naphthyl)indenyl)zirconium dichloride, dimethylsilanediyl(2,7-dimethyl-4-(p-t-butylphenyl)indenyl)(2-sec-butyl-4-(p-t-butylphenyl)indenyl)zirconium dichloride, dimethylsilanediyl(2,7-dimethyl-4-(p-t-butylphenyl)indenyl)(2-cyclobutyl-4-(p-t-butylphenyl)indenyl)zirconium dichloride, dimethylsilanediyl(2,7-dimethyl-4-(p-t-butylphenyl)indenyl)(2-(1-methylpropyl)-4-(p-t-butylphenyl)indenyl)zirconium dichloride, dimethylsilanediyl(2,7-dimethyl-4-(p-t-butylphenyl)indenyl)(2-(1-methylbutyl)-4-(p-t-butylphenyl)indenyl)zirconium dichloride, dimethylsilanediyl(2,7-dimethyl-4-(p-t-butylphenyl)indenyl)(2-(1-ethylbutyl)-4-(p-t-butylphenyl)indenyl)zirconium dichloride, dimethylsilanediyl(2,7-dimethyl-4-(p-t-butylphenyl)indenyl)(2-(1-methylpentyl)-4-(p-t-butylphenyl)indenyl)zirconium dichloride, dimethylsilanediyl(2,7-dimethyl-4-(p-t-butylphenyl)indenyl)(2-cyclopentyl-4-(p-t-butylphenyl)indenyl)zirconium dichloride, dimethylsilanediyl(2,7-dimethyl-4-(p-t-butylphenyl)indenyl)(2-cyclohexyl-4-(p-t-butylphenyl)indenyl)zirconium dichloride, dimethylsilanediyl(2,7-dimethyl-4-(p-t-butylphenyl)indenyl)(2-t-butyl-4-(p-t-butylphenyl)indenyl)zirconium dichloride, dimethylsilanediyl(2,7-dimethyl-4-(p-t-butylphenyl)indenyl)(2-(cyclopent-2-enyl)-4-(p-t-butylphenyl)indenyl)zirconium dichloride, dimethylsilanediyl(2,7-dimethyl-4-(p-t-butylphenyl)indenyl)(2-(cyclopent-3-enyl)-4-(p-t-butylphenyl)indenyl)zirconium dichloride, dimethylsilanediyl(2,7-dimethyl-4-(p-t-butylphenyl)indenyl)(2-cyclohex-2-enyl)-4-(p-t-butylphenyl)indenyl)zirconium dichloride, dimethylsilanediyl(2,7-dimethyl-4-(p-t-butylphenyl)indenyl)(2-(cyclohex-3-enyl)-4-(p-t-butylphenyl)indenyl)zirconium dichloride, dimethylsilanediyl(2,7-dimethyl-4-(p-t-butylphenyl)indenyl)(2-diphenylmethyl-4-(p-t-butylphenyl)indenyl)zirconium dichloride, dimethylsilanediyl(2,7-dimethyl-4-(p-t-butylphenyl)indenyl)(2-triphenylethyl-4-(p-t-butylphenyl)indenyl)zirconium dichloride, dimethylsilanediyl(2,7-dimethyl-4-(p-t-butylphenyl)indenyl)(2-phenyl-4-(p-t-butylphenyl)indenyl)zirconium dichloride, dimethylsilanediyl(2,7-dimethyl-4-(p-t-butylphenyl)indenyl)(2-(2-tolyl)-4-(p-t-butylphenyl)indenyl)zirconium dichloride, dimethylsilanediyl(2,7-dimethyl-4-(p-t-butylphenyl)indenyl)(2-(3-tolyl)-4-(p-t-butylphenyl)indenyl)zirconium dichloride, dimethylsilanediyl(2,7-dimethyl-4-(p-t-butylphenyl)indenyl)(2-(4-tolyl)-4-(p-t-butylphenyl)indenyl)zirconium dichloride, dimethylsilanediyl(2,7-dimethyl-4-(p-t-butylphenyl)indenyl)(2-(2,6-dimethylphenyl)-4-(p-t-butylphenyl)indenyl)zirconium dichloride, dimethylsilanediyl(2,7-dimethyl-4-(p-t-butylphenyl)indenyl)(2-(2,4,6-trimethylphenyl)-4-(p-t-butylphenyl)indenyl)zirconium dichloride, dimethylsilanediyl(2,7-dimethyl-4-(p-t-butylphenyl)indenyl)(2-(1-naphthyl)-4-(p-t-butylphenyl)indenyl)zirconium dichloride, dimethylsilanediyl(2,7-dimethyl-4-(p-t-butylphenyl)indenyl)(2-(2-naphthyl)-4-(p-t-butylphenyl)indenyl)zirconium dichloride, dimethylsilanediyl(2,7-dimethyl-4-(p-t-butylphenyl)indenyl)(2-phenanthrenyl-4-(p-t-butylphenyl)indenyl)zirconium dichloride, dimethylsilanediyl(2,7-dimethyl-4-(p-t-butylphenyl)indenyl)(2-trimethylsilyl-4-(p-t-butylphenyl)indenyl)zirconium dichloride, dimethylsilanediyl(2-ethyl-4-phenyl-7-methylindenyl)(2-isopropyl-4-phenylindenyl)zirconium dichloride, dimethylsilanediyl(4-phenyl-7-methylindenyl)(2-isopropyl-4-phenylindenyl)zirconium dichloride, dimethylsilanediyl(2-n-propyl-4-phenyl-7-methylindenyl)(2-isopropyl-4-phenylindenyl)zirconium dichloride, dimethylsilanediyl(2-n-butyl-4-phenyl-7-methylindenyl)(2-isopropyl-4-phenylindenyl)zirconium dichloride, dimethylsilanediyl(2-isobutyl-4-phenyl-7-methylindenyl)(2-isopropyl-4-phenylindenyl)zirconium dichloride, dimethylsilanediyl(2-n-pentyl-4-phenyl-7-methylindenyl)(2-isopropyl-4-phenylindenyl)zirconium dichloride, dimethylsilanediyl(2-benzyl-4-phenyl-7-methylindenyl)(2-isopropyl-4-phenylindenyl)zirconium dichloride, dimethylsilanediyl(2-phenylethyl-4-phenyl-7-methylindenyl)(2-isopropyl-4-phenylindenyl)zirconium dichloride, dimethylsilanediyl(2-ethyl-4-(1-naphthyl)-7-methylindenyl)(2-isopropyl-4-(1-naphthyl)indenyl)zirconium dichloride, dimethylsilanediyl(4-(1-naphthyl)-7-methylindenyl)(2-isopropyl-4-(1-naphthyl)indenyl)zirconium dichloride, dimethylsilanediyl(2-n-propyl-4-(1-naphthyl)-7-methylindenyl)(2-isopropyl-4-(1-naphthyl)indenyl)zirconium dichloride, dimethylsilanediyl(2-n-butyl-4-(1-naphthyl)-7-methylindenyl)(2-isopropyl-4-(1-naphthyl)indenyl)zirconium dichloride, dimethylsilanediyl(2-isobutyl-4-(1-naphthyl)-7-methylindenyl)(2-isopropyl-4-(1-naphthyl)indenyl)zirconium dichloride, dimethylsilanediyl(2-n-pentyl-4-(1-naphthyl)-7-methylindenyl)(2-isopropyl-4-(1-naphthyl)indenyl)zirconium dichloride, dimethylsilanediyl(2-benzyl-4-(1-naphthyl)-7-methylindenyl)(2-isopropyl-4-(1-naphthyl)indenyl)zirconium dichloride, dimethylsilanediyl(2-phenylethyl-4-(1-naphthyl)-7-methylindenyl)(2-isopropyl-4-(1-naphthyl)indenyl)zirconium dichloride, dimethylsilanediyl(2-ethyl-4-(p-t-butylphenyl)-7-methylindenyl)(2-isopropyl-4-(p-t-butylphenyl)indenyl)zirconium dichloride, dimethylsilanediyl(4-(p-t-butylphenyl)-7-methylindenyl)(2-isopropyl-4-(p-t-butylphenyl)indenyl)zirconium dichloride, dimethylsilanediyl(2-n-propyl-4-(p-t-butylphenyl)-7-methylindenyl)(2-isopropyl-4-(p-t-butylphenyl)indenyl)zirconium dichloride, dimethylsilanediyl(2-n-butyl-4-(p-t-butylphenyl)-7-methylindenyl)(2-isopropyl-4-(p-t-butylphenyl)indenyl)zirconium dichloride, dimethylsilanediyl(2-isobutyl-4-(p-t-butylphenyl)-7-methylindenyl)(2-isopropyl-4-(p-t-butylphenyl)indenyl)zirconium dichloride, dimethylsilanediyl(2-n-pentyl-4-(p-t-butylphenyl)-7-methylindenyl)(2-isopropyl-4-(p-t-butylphenyl)indenyl)zirconium dichloride, dimethylsilanediyl(2-benzyl-4-(p-t-butylphenyl)-7-methylindenyl)(2-isopropyl-4-(p-t-butylphenyl)indenyl)zirconium dichloride, dimethylsilanediyl(2-phenylethyl-4-(p-t-butylphenyl)-7-methylindenyl)(2-isopropyl-4-(p-t-butylphenyl)indenyl)zirconium dichloride, dimethylsilanediyl(2-methyl-4-phenyl-7-ethylindenyl)(2-isopropyl-4-phenylindenyl)zirconium dichloride, dimethylsilanediyl(2-methyl-4-phenyl-7-n-propylindenyl)(2-isopropyl-4-phenylindenyl)zirconium dichloride, dimethylsilanediyl(2-methyl-4-phenyl-7-n-butylindenyl)(2-isopropyl-4-phenylindenyl)zirconium dichloride, dimethylsilanediyl(2-methyl-4-phenyl-7-isopropylindenyl)(2-isopropyl-4-phenylindenyl)zirconium dichloride, dimethylsilanediyl(2-methyl-4-phenyl-7-t-butylindenyl)(2-isopropyl-4-phenylindenyl)zirconium dichloride, dimethylsilanediyl(2-methyl-4,7-diphenylindenyl)(2-isopropyl-4-phenylindenyl)zirconium dichloride, dimethylsilanediyl(2-methyl-4-phenyl-7-chloroindenyl)(2-isopropyl-4-phenylindenyl)zirconium dichloride, dimethylsilanediyl(2-methyl-4-phenyl-7-bromoindenyl)(2-isopropyl-4-phenylindenyl)zirconium dichloride, dimethylsilanediyl(2-methyl-4-phenyl-7-trifluoromethylindenyl)(2-isopropyl-4-phenylindenyl)zirconium dichloride, dimethylsilanediyl(2-methyl-4-(1-naphthyl)-7-ethylindenyl)(2-isopropyl-4-(1-naphthyl)indenyl)zirconium dichloride, dimethylsilanediyl(2-methyl-4-(1-naphthyl)-7-n-propylindenyl)(2-isopropyl-4-(1-naphthyl)indenyl)zirconium dichloride, dimethylsilanediyl(2-methyl-4-(1-naphthyl)-7-n-butylindenyl)(2-isopropyl-4-(1-naphthyl)indenyl)zirconium dichloride, dimethylsilanediyl(2-methyl-4-(1-naphthyl)-7-isopropylindenyl)(2-isopropyl-4-(1-naphthyl)indenyl)zirconium dichloride, dimethylsilanediyl(2-methyl- 4-(1-naphthyl)-7-t-butylindenyl)(2-isopropyl-4-(1-naphthyl)indenyl)zirconium dichloride, dimethylsilanediyl(2-methyl-4-(1-naphthyl)-7-phenylindenyl)(2-isopropyl-4-phenylindenyl)zirconium dichloride, dimethylsilanediyl(2-methyl-4-(1-naphthyl)-7-chloro-indenyl)(2-isopropyl-4-(1-naphthyl)indenyl)zirconium dichloride, dimethylsilanediyl(2-methyl-4-(1-naphthyl)-7-bromo-indenyl)(2-isopropyl-4-(1-naphthyl)indenyl)zirconium dichloride, dimethylsilanediyl(2-methyl-4-(1-naphthyl)-7-trifluoromethylindenyl)(2-isopropyl-4-(1-naphthyl)indenyl)zirconium dichloride, dimethylsilanediyl(2-methyl-4-(p-t-butylphenyl)-7-ethylindenyl)(2-isopropyl-4-(p-t-butylphenyl)indenyl)zirconium dichloride, dimethylsilanediyl(2-methyl-4-(p-t-butylphenyl)-7-n-propylindenyl)(2-isopropyl-4-(p-t-butylphenyl)indenyl)zirconium dichloride, dimethylsilanediyl(2-methyl-4-(p-t-butylphenyl)-7-n-butylindenyl)(2-isopropyl-4-(p-t-butylphenyl)indenyl)zirconium dichloride, dimethylsilanediyl(2-methyl-4-(p-t-butylphenyl)-7-isopropylindenyl)(2-isopropyl-4-(p-t-butylphenyl)indenyl)zirconium dichloride, dimethylsilanediyl(2-methyl-4-(p-t-butylphenyl)-7-t-butylindenyl)(2-isopropyl-4-(p-t-butylphenyl)indenyl)zirconium dichloride, dimethylsilanediyl(2-methyl-4-(p-t-butylphenyl)-7-phenylindenyl)(2-isopropyl-4-(p-t-butylphenyl)indenyl)zirconium dichloride, dimethylsilanediyl(2-methyl-4-(p-t-butylphenyl)-7-chloro-indenyl)(2-isopropyl-4-(p-t-butylphenyl)indenyl)zirconium dichloride, dimethylsilanediyl(2-methyl-4-(p-t-butylphenyl)-7-bromoindenyl)(2-isopropyl-4-(p-t-butylphenyl)indenyl)zirconium dichloride, dimethylsilanediyl(2-methyl-4-(p-t-butylphenyl)-7-trifluoromethylindenyl)(2-isopropyl-4-(p-t-butylphenyl)indenyl)zirconium dichloride, dimethylsilanediyl(2,5,7-trimethyl-4-phenylindenyl)(2-isopropyl-4-phenylindenyl)zirconium dichloride, dimethylsilanediyl(2,6,7-trimethyl-4-phenylindenyl)(2-isopropyl-4-phenylindenyl)zirconium dichloride, dimethylsilanediyl(2,5,6,7-tetramethyl-4-phenylindenyl)(2-isopropyl-4-phenylindenyl)zirconium dichloride, dimethylsilanediyl(2,5,7-trimethyl-4-(1-naphthyl)indenyl)(2-isopropyl-4-(1-naphthyl)indenyl)zirconium dichloride, dimethylsilanediyl(2,6,7-trimethyl-4-(1-naphthyl)indenyl)(2-isopropyl-4-(naphthyl)indenyl)zirconium dichloride, dimethylsilanediyl(2,5,6,7-tetramethyl-4-(1-naphthyl)indenyl)(2-isopropyl-4-(1-naphthyl)indenyl)zirconium dichloride, dimethylsilanediyl(2,5,7-trimethyl-4-(p-t-butylphenyl)indenyl)(2-isopropyl-4-(p-t-butylphenyl)indenyl)zirconium dichloride, dimethylsilanediyl(2,6,7-trimethyl-4-(p-t-butylphenyl)indenyl)(2-isopropyl-4-(p-t-butylphenyl)indenyl)zirconium dichloride, dimethylsilanediyl(2,5,6,7-tetramethyl-4-(p-t-butylphenyl)indenyl)(2-isopropyl-4-(p-t-butylphenyl)indenyl)zirconium dichloride, dimethylsilanediyl(2,5,7trimethyl-4-(1-naphthyl)indenyl)(2-isopropyl-4-phenylindenyl)zirconium dichloride, dimethylsilanediyl(2,6,7-trimethyl-4-(1-naphthyl)indenyl)(2-isopropyl-4-phenylindenyl)zirconium dichloride, dimethylsilanediyl(2,5,6,7-tetramethyl-4-(1-naphthyl)indenyl)(2-isopropyl-4-phenylindenyl)zirconium dichloride, dimethylsilanediyl(2,5,7-trimethyl-4-(p-t-butylphenyl)indenyl)(2-isopropyl-4-phenylindenyl)zirconium dichloride, dimethylsilanediyl(2,6,7-trimethyl-4-(p-t-butylphenyl)indenyl)(2-isopropyl-4-phenylindenyl)zirconium dichloride, dimethylsilanediyl(2,5,6,7-tetramethyl-4-(p-t-butylphenyl)indenyl)(2-isopropyl-4-phenylindenyl)zirconium dichloride, dimethylsilanediyl(2,5,7-trimethyl-4-(1-naphthyl)indenyl)(2-isopropyl-4-(p-t-butylphenyl)indenyl)zirconium dichloride, dimethylsilanediyl(2,6,7-trimethyl-4-(1-naphthyl)indenyl)(2-isopropyl-4-(p-t-butylphenyl)indenyl)zirconium dichloride, dimethylsilanediyl(2,5,6,7-tetramethyl-4-(1-naphthyl)indenyl)(2-isopropyl-4-(p-t-butylphenyl) indenyl)zirconium dichloride.

dimethylgermanediyl(2,7-dimethyl-4-phenylindenyl)(2-isopropyl-4-phenylindenyl)zirconium dichloride, ethylidene (2,7-dimethyl-4-phenylindenyl)(2-isopropyl-4-phenylindenyl)zirconium dichloride, dimethylmethylidene(2,7-dimethyl-4-phenylindenyl)(2-isopropyl-4-phenylindenyl) zirconium dichloride, methylidene(2,7-dimethyl-4-phenylindenyl)(2-isopropyl-4-phenylindenyl)zirconium dichloride, diphenylmethylidene(2,7-dimethyl-4-phenylindenyl)(2-isopropyl-4-phenylindenyl)zirconium dichloride, dimethylgermanediyl(2,7-dimethyl-4-(1-naphthyl)indenyl)(2-isopropyl-4-(1-naphthyl)indenyl)zirconium dichloride, ethylidene(2,7-dimethyl-4-(1-naphthyl)indenyl)(2-isopropyl-4-(1-naphthyl)indenyl)zirconium dichloride, dimethylmethylidene(2,7-dimethyl-4-(1-naphthyl)indenyl) (2-isopropyl-4-(1-naphthyl)indenyl)zirconium dichloride, methylidene(2,7-dimethyl-4-(1-naphthyl)indenyl)(2-isopropyl-4-(1-naphthyl)indenyl)zirconium dichloride, diphenylmethylidene(2,7-dimethyl-4-(1-naphthyl)indenyl)(2-isopropyl-4-(1-naphthyl)indenyl)zirconium dichloride, dimethylgermanediyl(2,7-dimethyl-4-(p-t-butylphenyl) indenyl)(2-isopropyl-4-(p-t-butylphenyl)indenyl)zirconium dichloride, ethylidene(2,7-dimethyl-4-(p-t-butylphenyl)indenyl)(2-isopropyl-4-(p-t-butylphenyl)indenyl)zirconium dichloride, dimethylmethylidene(2,7-dimethyl-4-(p-t-butylphenyl)indenyl)(2-isopropyl-4-(p-t-butylphenyl)indenyl) zirconium dichloride, methylidene(2,7-dimethyl-4-(p-t-butylphenyl)indenyl)(2-isopropyl-4-(p-t-butylphenyl)indenyl) zirconium dichloride und diphenylmethylidene(2,7-dimethyl-4-(p-t-butylphenyl)indenyl)(2-isopropyl-4-(p-t-butylphenyl)indenyl)zirconium dichloride.

The metallocenes of the present invention can be prepared by methods such as those described in WO 01/48034.

The invention further provides biscyclopentadienyll ligand systems of the formula (II)

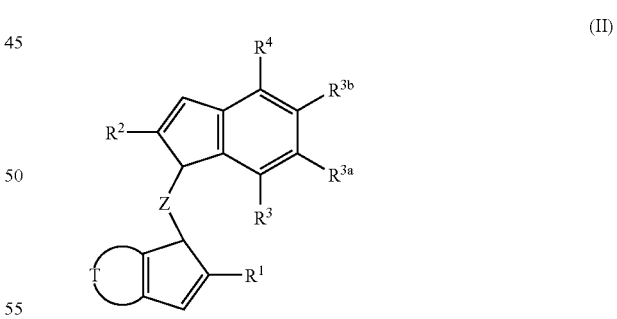

(II)

or its double bond isomers, where the variables $R^1$, $R^2$, $R^3$, $R^{3a}$, $R^{3b}$, $R^4$, T and Z are as defined under formula (I).

Particular preference is given to biscyclopentadienyl ligand systems of the formula (II) or its double bond isomers in which $R^3$, $R^{3a}$ are identical or different and are each hydrogen or a $C_1$–$C_{40}$ radical, where at least one of the radicals $R^3$ and $R^{3a}$ is not hydrogen, $R^{3b}$ is hydrogen, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (I).

Also particular preference is given to biscyclopentadienyl ligand systems of the formula (II) or its double bond isomers in which $R^3$ is a $C_1$–$C_{40}$ radical $R^{3a}$, $R^{3b}$ are identical or different and are each hydrogen or a $C_1$–$C_{40}$ radical T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (I).

The substitution pattern of the biscyclopentadienyl ligand systems of the formula (II) is critical to the particular polymerization properties of the organometallic transition metal compounds containing these biscyclopentadienyl ligand systems.

The invention therefore also provides for the use of a biscyclopentadienyl ligand system of the formula (II) for preparing an organometallic transition metal compound, preferably for preparing an organometallic transition metal compound containing an element of group 4 of the Periodic Table of the Elements, in particular zirconium.

The novel organometallic transition metal compounds of the formulae (I), (Ia), (Ib) and (Ic) are, especially in the presence of suitable cocatalysts, highly active catalyst constituents for the polymerization of olefins.

The present invention therefore also provides a catalyst system comprising at least one organometallic transition metal compound of the formula (I), (Ia), (Ib) or (Ic) and at least one cocatalyst B).

Together with the organometallic transition metal compound of the present invention, the cocatalyst (B) forms a polymerization-active catalyst system, with the cocatalyst acting as cation-forming compound.

Suitable cation-forming compounds B) which are able to react with an organometallic transition metal compound according to the present invention to convert it into a cationic compound are, for example, aluminoxanes, strong uncharged Lewis acids, ionic compounds having an Lewis-acid cation and ionic compounds having a Brönsted acid as cation. In the case of metallocene complexes as organometallic transition metal compound, the cation-forming compounds B) are frequently also referred to as compounds capable of forming metallocenium ions.

As aluminoxanes, it is possible to use, for example, the compounds described in WO 00/31090. Particularly useful compounds of this type are open-chain or cyclic aluminoxane compounds of the formula (V) or (VI)

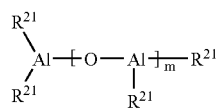

(V)

-continued

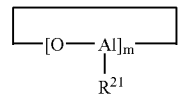

(VI)

where $R^{21}$ is a $C_1$–$C_4$-alkyl group, preferably a methyl or ethyl group, and m is an integer from 5 to 30, preferably from 10 to 25.

These oligomeric aluminoxane compounds are usually prepared by reacting a solution of a trialkylaluminum with water. In general, the oligomeric aluminoxane compounds obtained in this way are in the form of mixtures of both linear and cyclic chain molecules of various lengths, so that m is to be regarded as a mean. The aluminoxane compounds can also be present in admixture with other metal alkyls, preferably aluminum alkyls.

Furthermore, in place of the aluminoxane compounds of the formula (V) or (VI), it is also possible to use modified aluminoxanes in which some of the hydrocarbon radicals or hydrogen atoms are replaced by alkoxy, aryloxy, siloxy or amide radicals as component B).

It has been found to be advantageous to use the organometallic transition metal compound of the present invention and the aluminoxane compounds in such amounts that the atomic ratio of aluminum from the aluminoxane compounds to the transition metal from the organometallic transition metal compound is in the range from 10:1 to 1000:1, preferably from 20:1 to 500:1 and in particular from 30:1 to 400:1.

As strong, uncharged Lewis acids, preference is given to compounds of the formula (VII)

$$M^3X^1X^2X^3 \qquad (VII)$$

where $M^3$ is an element of group 13 of the Periodic Table of the Elements, in particular B, Al or Ga, preferably B, $X^1$, $X^2$ and $X^3$ are each hydrogen, $C_1$–$C_{10}$-alkyl, $C_6$–$C_{15}$-aryl, alkylaryl, arylalkyl, haloalkyl or haloaryl each have from 1 to 10 carbon atoms in the alkyl radical and from 6 to 20 carbon atoms in the aryl radical or fluorine, chlorine, bromine or iodone, in particular haloaryls, preferably pentafluorophenyl.

Further examples of strong, uncharged Lewis acids are mentioned in WO 00/31090.

Particular preference is given to compounds of the formula (VII) in which $X^1$, $X^2$ and $X^3$ are identical, preferably tris(pentafluorophenyl)borane.

Further strong uncharged Lewis acids which are suitable as cation-forming compounds B) are the reaction products from the reaction of a boronic acid with two equivalents of a trialkylaluminum or the reaction products from the reaction of a trialkylaluminum with two equivalents of an acidic, fluorinated, in particular perfluorinated, carbon compound such as pentafluorophenol or bis(pentafluorophenyl)borinic acid.

Suitable ionic compounds having Lewis-acid cations are salt-like compounds of the cation of the formula (VIII)

$$[(Y^{a+})Q_1Q_2 \ldots Q_z]^{d+} \qquad (VIII)$$

where

Y is an element of groups 1 to 16 of the Periodic Table of the Elements, $Q_1$ to $Q_z$ are singly negatively charged groups such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$–$C_{10}$-cycloalkyl which may bear $C_1$–$C_{10}$-alkyl groups as substituents, halogen, $C_1$–$C_{28}$-alkoxy, $C_6$–$C_{15}$-aryloxy, silyl or mercaptyl groups a is an integer from 1 to 6 and z is an integer from 0 to 5, d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts containing noncoordinating anions can also be prepared by combining a boron or aluminum compound, e.g. an aluminum alkyl, with a second compound which can react so as to link two or more boron or aluminum atoms, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, can be added.

Ionic compounds having Brönsted acids as cations preferably likewise have noncoordinating counterions. As Brönsted acid, particular preference is given to protonated amine or aniline derivatives. Preferred cations are N,N-dimethylanilinium, N,N-dimethylcylohexylammonium and N,N-dimethylbenzylammonium and also derivatives of the latter two.

Preferred ionic compounds B) are, in particular, N,N-dimethylanilinium tetrakis(pentafluorophenyl)-borate, N,N-dimethylcyclohexylammonium tetrakis(pentafluorophenyl)borate and N,N-dimethyl-benzylammonium tetrakis(pentafluorophenyl)borate.

It is also possible for two or more borate anions to be joined to one another, as in the dianion $[(C_6F_5)_2B-C_6F_4-B(C_6F_5)_2]^{2-}$, or the borate anion can be bound to a support surface via a bridge having a suitable functional group.

Further suitable cation-forming compounds B) are listed in WO 00/31090.

The amount of strong, uncharged Lewis acids, ionic compounds having Lewis-acid cations or ionic compounds having Brönsted acids as cations is preferably from 0.1 to 20 equivalents, more preferably from 1 to 10 equivalents, based on the organometallic transition metal compound of the present invention.

Further suitable cation-forming compounds B) are boron-aluminum compounds such as di[bis(pentafluorophenyl)boroxy]methylalane. Boron-aluminum compounds of this type are disclosed, for example in WO 99/06414.

It is also possible to use mixtures of all the abovementioned cation-forming compounds B). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the organometallic transition metal compound of the present invention and the cation-forming compounds B) in a solvent, with aromatic hydrocarbons having from 6 to 20 carbon atoms, in particular xylene and toluene, being preferred.

The catalyst can further comprise, as additional component C), a metal compound of the formula (IX), $$M^4(R^{22})_r(R^{23})_s(R^{24})_t \tag{IX}$$

where $M^4$ is an alkali metal, an alkaline earth metal or metal of group 13 of the Periodic Table, i.e. boron, aluminum, gallium, indium or thallium, $R^{22}$ is hydrogen, $C_1$–$C_{10}$alkyl, $C_6$–$C_{15}$-aryl, alkylaryl or arylalkyl each having from 1 to 10 carbon atoms in the alkyl part and from 6 to 20 carbon atoms in the aryl part, $R^{23}$ and $R^{24}$ are each hydrogen, halogen, $C_1$–$C_{10}$-alkyl, $C_6$–$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3 and s and t are integers from 0 to 2, where the sum r+s+t corresponds to the valence of $M^4$, where the component C) is not identical to the component B). It is also possible to use mixtures of various metal compounds of the formula (IX).

Among the metal compounds of the formula (IX), preference is given to those in which $M^4$ is lithium, magnesium or aluminum and $R^{23}$ and $R^{24}$ are each $C_1$–$C_{10}$-alkyl.

Particularly preferred metal compounds of the formula (IX) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

If a metal compound C) is used, it is preferably present in the catalyst in such an amount that the molar ratio of $M^4$ from formula (IX) to transition metal $M^1$ from the organometallic transition metal compound of the present invention is from 800:1 to 1:1, in particular from 200:1 to 2:1.

Further useful cocatalyst systems B) are combinations obtained by combining the following compounds:

1. at least one defined boron or aluminum compound,
2. at least one uncharged compound having at least one acidic hydrogen atom,
3. at least one support, preferably an inorganic oxidic support, and
4. optionally a base, preferably an organic nitrogen-containing base such as an amine, an aniline derivative or a nitrogen heterocycle.

The boron or aluminum compound used in the preparation of the supported cocatalysts is preferably a compound of the formula X

where $R^{70}$ are identical or different and are each a hydrogen atom, a halogen atom, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl or an $OSiR^{77}_3$ group, where $R^{77}$ are identical or different and are each a hydrogen atom, a halogen atom, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$- aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl, preferably hydrogen, $C_1$–$C_8$-alkyl or $C_7$–$C_{20}$-arylalkyl, and $M^5$ is boron or aluminum, preferably aluminum.

Particularly preferred compounds of the formula X are trimethylaluminum, triethylaluminum and triisobutylaluminum.

The uncharged compounds which have at least one acidic hydrogen atom and can react with compounds of the formula (X) are preferably compounds of the formulae XI, XII and XIII, $$R^{71}\text{-D-H} \quad (XI)$$

$$(R^{71})_{3-h}\text{—B-(D-H)}_h \quad (XII)$$

$$\text{H-D-}R^{72}\text{-D-H} \quad (XIII)$$

where $R^{71}$ are identical or different and are each a hydrogen atom, a halogen atom, a boron-free $C_1$–$C_{40}$ group such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl, or an $Si(R^{73})_3$ group or a $CH(SiR^{73}_3)_2$ group, where $R^{73}$ is a boron-free $C_1$–$C_{40}$ group such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalky, $C_7$–$C_{40}$-haloarylalky, $C_7$–$C_{40}$-alkylaryl, $C_7$–$C_{40}$-haloalkylaryl, and $R^{72}$ is a divalent $C_1$–$C_{40}$ group such as $C_1$–$C_{20}$-alkylene, $C_1$–$C_{20}$-haloalkylene, $C_6$–$C_{20}$-arylene, $C_6$–$C_{20}$-haloarylene, $C_7$–$C_{40}$-arylalkylene, $C_7$–$C_{40}$-haloarylalkylene, $C_7$–$C_{40}$-alkylarylene, $C_7$–$C_{40}$-haloalkylarylene, D is an element of group 16 of the Periodic Table of the Elements or an $NR^{74}$ group, where $R^{74}$ is a hydrogen atom or a $C_1$–$C_{20}$-hydrocarbon radical such as $C_1$–$C_{20}$-alkyl or $C_6$–$C_{20}$-aryl, preferably oxygen, and h is 1 or 2.

Suitable compounds of the formula (XI) include water, alcohols, phenol derivatives, thiophenol derivatives and aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl.

Suitable compounds of the formula (XII) include boronic acids and borinic acids, in particular borinic acids having perfluorinated aryl radicals, for example $(C_6F_5)_2BOH$. Suitable compounds of the formula (XIII) include dihydroxy compounds in which the divalent carbon-containing group is preferably halogenated, in particular perfluorinated. An example of such a compound is 4,4'-dihydroxy-2,2',3,3',5,5',6,6'-octafluorobiphenyl hydrate.

Examples of combinations of compounds of the formula (X) with compounds of the formula (XI) or (XIII) are trimethylaluminum/pentafluorophenol, trimethylaluminum/1-bis(pentafluorophenyl)methanol, trimethylaluminum/4-hydroxy-2,2',3,3',4,4',5,5',6,6'-nonafluorobiphenyl, triethylaluminum/pentafluorophenol and triisobutylaluminum/pentafluorophenol and triethylaluminum/4,4'-dihydroxy-2,2',3,3',5,5',6,6'-octafluorobiphenyl hydrate, with, for example, reaction products of the following types being able to be formed.

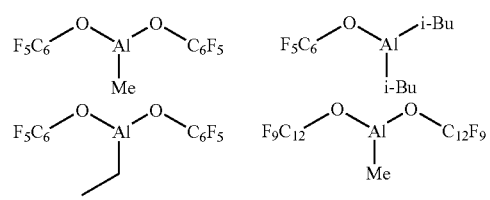

Examples of reaction products of the reaction of at least one compound of the formula (X) with at least one compound of the formula (XII) are:

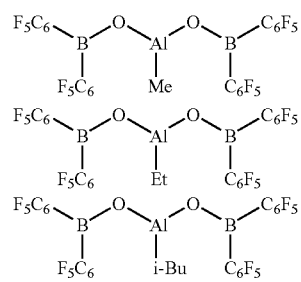

In principle, the components can be combined in any desired manner.

If desired, the reaction products of the reaction of at least one compound of the formula X with at least one compound of the formula XI, XII or XIII and optionally the organic nitrogen base may additionally be combined with an organometallic compound of the formula V, VI, VII and/or IX so as to form, together with the support, the supported cocatalyst system B).

In a preferred variant, the components 1 (formula X) and 2 (formula XI, XII or XIII) and also the components 3 (support) and 4 (base) are combined separately and subsequently reacted with one another, with the reaction preferably taking place in an inert solvent or suspension medium. The supported cocatalyst B) formed can be freed of the inert solvent or suspension medium before it is reacted with the organometallic transition metal component of the present invention and, if desired, the component C).

Particular preference is given to a catalyst system comprising an organometallic transition metal compound according to the present invention and at least one cocatalyst B) which further comprises a support component D).

To obtain such a supported catalyst system, the unsupported catalyst system can be reacted with a support component D). In principle, the order in which support component D), organometallic transition metal compound according to the present invention and cocatalyst B) are combined is immaterial. The organometallic transition metal compound of the present invention and the cocatalyst B) can be immobilized independently or simultaneously. After the individual process steps, the solid can be washed with suitable inert solvents such as aliphatic or aromatic hydrocarbons.

As support component D), preference is given to using finely divided supports which may be any organic or inorganic, inert solvents. In particular, the support component D) can be a porous support such as talc, a sheet silicate, an inorganic oxide or a finely divided polymer powder (e.g. polyolefin).

Suitable inorganic oxides may be found among oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium and titanium and also corresponding oxide mixtures. Other inorganic oxides which can be used either alone or in combination with the abovementioned preferred oxidic supports are, for example, MgO, $ZrO_2$, $TiO_2$ or $B_2O_3$. An example of a preferred mixed oxide is calcined hydrotalcite.

The support materials used preferably have a specific surface area in the range from 10 to 1000 $m^2/g$, a pore volume in the range from 0.1 to 5 ml/g and a mean particle size of from 1 to 500 µm. Preference is given to supports having a specific surface area in the range from 50 to 500 $m^2/g$, a pore volume in the range from 0.5 to 3.5 ml/g and a mean particle size in the range from 5 to 350 µm. Particular preference is given to supports having a specific surface area in the range from 200 to 400 $m^2/g$, a pore volume in the range from 0.8 to 3.0 ml/g and a mean particle size of from 10 to 100 µm.

The inorganic support can be subjected to a thermal treatment, for example to remove adsorbed water. Such a drying treatment is generally carried out at from 80 to 300° C., preferably from 100 to 200° C., with drying at 100–200° C. preferably being carried out under reduced pressure and/or under a blanket of inert gas (e.g. nitrogen), or the inorganic support can be calcined at from 200 to 1000° C. to produce, if necessary, the desired structure of the solid and/or the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090. The inorganic support material can also be modified chemically. For example, treatment of silica gel with $NH_4SiF_6$ leads to fluorination of the silica gel surface or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrenes, via whose functional groups, for example ammonium or hydroxy groups, at least one of the catalyst components can be immobilized.

In a preferred embodiment of the preparation of the supported catalyst system, at least one of the organometallic transition metal compounds of the present invention is brought into contact with at least one cocatalyst component B) in a suitable solvent, preferably giving a soluble reaction product, an adduct or a mixture.

The preparation obtained this way is then mixed with the dehydrated or passivated support material, the solvent is removed and the resulting supported organometallic transition metal catalyst system is dried to ensure that the solvent is completely or mostly removed from the pores of the support material. The supported catalyst is obtained as a free-flowing powder. Examples of industrial implementation of the above process are described in WO 96/00243, WO 98/40419 or WO 00/05277. A further preferred embodiment is firstly to apply the cation-forming compound B) to the support component and subsequently to bring this supported cation-forming compound into contact with the organometallic transition metal compound of the present invention.

It is also possible firstly to prepolymerize the catalyst solid with α-olefins, preferably linear $C_2$–$C_{10}$-1-alkenes, in particular ethylene or propylene, and then to use the resulting prepolymerized catalyst solid in the actual polymerization. The molar ratio of catalyst solid used in the prepolymerization to monomer polymerized onto it is usually in the range from 1:0.1 to 1:200.

Furthermore, a small amount of an olefin, preferably an α-olefins, for example vinylcyclohexane, styrene or phenyldimethylvinylsilane, as modifying component, an antistatic or a suitable inert compound such as wax or oil can be added as additive during or after the preparation of the supported catalyst system. The molar ratio of additives to organometallic transition metal compound of the present invention is usually from 1:1000 to 1000:1, preferably from 1:5 to 20:1.

The novel organometallic transition metal compounds of the formulae (I), (Ia), (Ib) and (Ic) or the catalyst systems in which they are present are suitable for the polymerization or copolymerization of olefins.

The present invention therefore also provides a process for preparing polyolefins by polymerization or copolymerization of at least one olefin in the presence of a catalyst system comprising at least one of the novel organometallic transition metal compounds of the formulae (I), (II), (IIa), (IIb) and (IIc).

In general, the catalyst system is used together with a further metal compound C') of the formula (IX), where this component may be different from the metal compound(s) C) used for preparing the catalyst system, as constituent of a catalyst system for the polymerization or copolymerization of olefins. It is also possible to add one or more further cation-forming compounds B) to the catalyst system during the polymerization process.

Olefins can be functionalized, olefinically unsaturated compounds such as ester or amide derivatives of acrylic or methacrylic acid, for example, acrylates, methacrylates or acrylonitrile, or nonpolar olefinic compounds, including aryl-substituted α-olefins.

Preference is given to polymerizing olefins of the formula $R_m$—CH═CH—$R_n$, where $R_m$ and $R_n$ are identical or different and are each a hydrogen atom or an organic radical having from 1 to 20 carbon atoms, in particular from 1 to 10 carbon atoms, and $R_m$ and $R_n$ together with the atoms connecting them may form one or more rings.

Examples of such olefins are 1-olefins having from 2 to 40, preferably from 2 to 10, carbon atoms, e.g. ethene, propene, 1-butene, 1-pentene, 1-hexene, 1-heptene, 1-octene, 1-decene or 4-methyl-1-pentene or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene.

The catalyst system of the present invention is particularly preferably used for homopolymerizing propene or ethene or copolymerizing ethene with $C_3$–$C_8$-α-olefins such as propene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene, and very particularly preferably for copolymerizing propene with ethylene and/or 1-butene. Examples of such copolymers are propene-ethene copolymers, propene-1-butene copolymers, ethene-1-hexene copolymers, ethene-1-octene copolymers, ethene-propene-ethylidenenorbornene terpolymers and ethene-propen-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are possible. As solvents or suspension media, it is possible to use inert hydrocarbons, for example isobutane, or else the monomers themselves.

The polymerization can be carried out at from −60 to 300° C. and pressures in the range from 0.5 to 3000 bar. Preference is given to temperatures in the range from 50 to 200° C., in particular from 60 to 100° C., and pressures in the range from 5 to 100 bar, in particular from 15 to 70 bar. The mean residence times are usually from 0.5 to 5 hours, preferably from 0.5 to 3 hours. It is also possible to use molar mass regulators, for example hydrogen, or customary additives such as antistatics in the polymerization. To carry out the polymerization, the catalyst system of the present invention can be used directly, i.e. it is introduced in undiluted form into the polymerization system, or it is admixed with inert components such as paraffins, oils or waxes to improve the meterability.

The organometallic transition metal compounds of the formulae (I), (Ia), (Ib) and (Ic) or the catalyst systems in which they are present are especially useful for preparing polypropylene/propylene-ethylene copolymer mixtures.

Accordingly, the invention further provides a process for preparing polypropylene/propylene-ethylene copolymer mixtures in the presence of a catalyst system as described above.

The polymers prepared using the catalyst system of the present invention (hereinafter also referred to as (co)polymers) display a uniform particle morphology and contain no fines. In the polymerization using the catalyst system of the present invention, no deposits or cake material are formed on the reactor components.

The (co)polymers obtainable using the catalyst system of the present invention include both. homopolymers and random copolymers of propylene. Their molar mass $M_w$ (measured by gel permeation chromatography) is in the range from 100000 to 1000000 g/mol and their $M_w/M_n$ (measured by gel permeation chromatography) is in the range from 1.8 to 4.0, preferably from 1.8 to 3.5. Random copolymers of propylene contain subordinate amounts of monomers which can be copolymerized with propylene, for exampe $C_2$–$C_8$-alk-1-enes such as ethylene, 1-butene, 1-pentene, 1-hexene or 4-methyl-1-pentene. It is also possible to use two or more different comonomers, which then results in, for example, random terpolymers.

The catalyst system of the present invention is particularly useful for preparing homopolymers of propylene or copolymers of propylene with up to 50% by weight of other copolymerized 1-alkenes having up to 8 carbon atoms. The copolymers of propylene can be random copolymers or block or high-impact copolymers. If the copolymers of propylene have a random structure, they generally contain up to 50% by weight, preferably up to 15% by weight, particularly preferably up to 1% by weight, of other 1-alkenes having up to 8 carbon atoms, in particular ethylene, 1-butene, 4-methyl-1-pentene or a mixture of ethylene and 1-butene, ethylene and 1-hexene or ethylene and 4-methyl-1-pentene.

The copolymers prepared using the catalyst system of the present invention can also be block or high-impact copolymers of propylene, in the case of which a propylene homopolymer or random copolymer of propylene with from 0.001 to 15% by weight, preferably from 0.01 to 6% by weight, of other 1-alkenes having up to 8 carbon atoms (e.g. ethylene, 1-butene, 1-hexene, 1-octene, 4-methyl-1-pentene) is prepared in a first step and a propylene-ethylene copolymer which has an ethylene content of from 15 to 80% by weight and may further comprise other $C_4$–$C_8$-alk-1-enes (e.g. ethylene, 1-butene, 1-hexene, 1-octene, 4-methyl-1-pentene) is copolymerized onto this in a second step. In general, the amount of propylene-ethylene copolymer (which may further comprise ethylene, 1-butene, 1-hexene, 1-octene, 4-methyl-1-pentene as additional comonomers) copolymerized onto the first polymer is such that the copolymer produced in the second step makes up from 3 to 60% by weight of the end product.

The propylene homopolymers and copolymers prepared using the catalyst system of the present invention have a content of meso-configured diads (measured by $^{13}$C-NMR spectroscopy, see examples) of at least 90%, preferably at least 95% and particularly preferably at least 98%.

Random copolymers produced using single-site catalysts (e.g. metallocene catalysts) have a series of advantages over, for example, Ziegler-Natta-catalyst copolymers having a comparable comonomer content.

Thus, single-site-catalyzed copolymers have a uniform comonomer distribution over their molar mass range. Such a distribution can be determined, for example, by means of a coupled GPC-IR measurement.

In single-site-catalyzed copolymers, the comonomers are randomly distributed, while Ziegler-Natta-catalyzed copolymers tend to incorporate the comonomer in blocks even at low comonomer contents. It fluctuates little as long as the fractions make up a sufficiently large proportion (at least 10%) of the total polymer. In the case of copolymers prepared according to the present invention, the comonomer content fluctuates by not more than 10%, preferably not more than 5%, particularly preferably not more than 1.5% between the fractions which are sufficiently large.

Single-site-catalyzed copolymers have a narrow molar mass distribution ex reactor ($M_w/M_n$ is generally <=3.0). Ziegler-Natta-catalyzed copolymers have broader molar mass distribution ex reactor.

In addition, single-site-catalyzed copolymers have a low proportion of soluble material. At a copolymerized ethylene content of 10 mol %, the proportion of ether-soluble material is less than 5%.

Furthermore, a combination of the abovementioned features leads to the polymers (homopolymers and copolymers) prepared using the catalyst system of the present invention being eluted within a narrow temperature range in a TREF. In the case of the homopolymers and random copolymers prepared using the catalyst system of the present invention, from 80 to 100% by weight is eluted within a temperature interval extending from 15° C. below to 15° C. above the temperature of maximum elution (peak temperature). The range preferably extends from 15° C. below to 10° C. above the peak temperature and particularly preferably from 10° C. below to 10° C. above the peak temperature.

The polymers (homopolymers and copolymers) prepared using the catalyst system of the present invention are suitable for producing hard and stiff shaped bodies, fibers, filaments, injection molded parts, films, sheets or large hollow bodies (e.g. pipes) having a high tensile strength. The moldings display, in particular, a high toughness, even at below 20° C., in combination with high stiffness.

Shaped bodies (e.g. injection-molded articles) made of the block or high-impact copolymers prepared using the catalyst system of the present invention are generally produced by the customary injection-molding methods known to those skilled in the art and have a novel property combination of stiffness, toughness and transparency and, in addition, display little stress whitening.

The E modulus, as a measure of the stiffness of the copolymers prepared using the catalyst system of the present invention, measured in a tensile test in accordance with ISO 527, is generally in the range from 500 to 6000 MPa, preferably in the range from 800 to 2000 MPa, very particularly preferably in the range from 900 to 1400 MPa.

The Charpy impact toughness, as a measure of the toughness of the copolymers prepared using the catalyst system of the present invention, measured in accordance with ISO 179-2/1eU, is >200 kJ/m$^2$ at 23° C. and >20 kJ/m$^2$ at −20° C. At 23° C., it is preferred that no fracture of the test specimen is recorded.

The haze, as complementary parameter to the transparency (% transparency+% haze=100%), determined in accordance with ASTM D 1003, of the copolymers prepared using the catalyst system of the present invention is preferably is less than 40%, particularly preferably less than 30%.

The injection-molded articles produced from the above-described polymers may further comprise customary thermoplastics additives in the customary amounts. Possible additives are antistatics, lubricants such as fatty acid amides, for example erucamide, stabilizers, fire retardants, neutralizing agents such as calcium stearate, pigments, dyes such as pigment dyes or liquid dyes, carbon black and also inorganic fillers such as talc, chalk, aluminum oxide, aluminum sulfate, barium sulfate, calcium magnesium carbonate, silicon dioxide, titanium dioxide, glass fibers and organic fillers such as polyester, polystyrene, polyamide and halogenated organic polymers.

Further preferred additives are nucleating agents such as talc, alkali metal, alkaline earth metal or aluminum salts of alkylcarboxylic, arylcarboxylic, arylalkylcarboxylic or alkylarylcarboxylic acids, particular polymers such as polyvinylcyclohexane or polycyclopentene, and also polyhydroxy compounds such as sorbitol derivatives. Preference is given to talc, aluminum salts, alkali metal salts and alkaline earth metal salts of cyclic arylalkylcarboxylic acids, and sorbitol derivatives. Particular preference is given to sorbitol derivatives.

EXAMPLES

General

The letter "c" at the beginning of an experiment number or designation of a substance indicates experiments or substances which are not according to the present invention and are included for comparison.

Preparation of the Catalyst:

0.206 mmol of a metallocene dichloride was added at room temperature to 4.33 mmol of MAO (30% strength by weight solution in toluene, manufactured by Albemarle). The solution was allowed to stand overnight at room temperature and was subsequently diluted with 10.9 ml of toluene. The dilute solution was carefully added to 10 g of silica (Sylopol 948 calcined at 600° C., manufactured by Grace). Particular attention was paid to obtaining a uniform distribution of the colored solution over the support material. After 10 minutes, the flask containing the catalyst suspension was connected to a vacuum line and dried on the vacuum line until the volatiles content had been reduced to less than 5% by weight.

Polymerizations:

1. Homopolymer

Homopolymerizations were carried out in a 16 l reactor charged with 10 l of liquid propene or in a 5 l reactor charged with 3 l of liquid propene. The reactors were blanketed with nitrogen prior to filling. A 20% strength by weight solution of triethylaluminum in Exxsol (from Witco) was introduced into the reactors (8 ml into the large reactor, 2.4 ml into the small reactor) and the mixtures were stirred at 30° C. for 15 minutes. If hydrogen was added, its concentration was set to 0.5 standard liters per liter of liquid propylene. A suspension of the respective catalyst in 20 ml of Exxsol was introduced into the reactors. The reactor temperature was increased to 65° C. and held at this temperature for 60 minutes. The polymerizations were stopped by venting the reactor. The polymers were dried overnight under reduced pressure before being analyzed.

2. Impact Copolymer

Impact copolymers were produced by a two-step procedure in a 24 l reactor charged with 10 l of liquid propylene. A homopolymerization without hydrogen (procedure as described above) was followed by addition of 10 bar of ethylene. Reactor pressure and temperature were kept constant for another 30 minutes. The reactor was vented and the polymer blend produced was dried under reduced pressure.

Fractionation of the Polymer Blends:

The polymer blends from the copolymerization were fractionated as follows: 5 g of the polymer blend was suspended in 1 l of Exxsol 140/170 (stabilized with 0.1% of Irganox 1010 and deoxygenated by passing nitrogen through it before use). While stirring slowly and under nitrogen, the suspension was dissolved by heating to 130° C. At a stirrer speed of 350 rpm, the solution was cooled to 50° C. and held at this temperature for 15 minutes. The crystallized polymer was isolated on a filter, the supernatant solution was removed and the remaining solid was washed with small amounts of Exxsol. The dissolution/crystallization procedure was repeated one more time. The "crystallized fraction" was isolated on a D3 frit and dried under reduced pressure. The Exxsol solutions from the filtration and washing steps were combined and evaporated to a volume of about 250 ml. The dissolved polymer was precipitated with 1 l of acetone and isolated on a D1 frit. The moist polymer was refluxed with 280 ml of diethyl ether (stabilized with 0.1% of Irganox 1010) for 4 hours. The "(amorphous) ether-insoluble fraction" which remained was isolated on a D3 frit and dried under reduced pressure.

The ether solution was evaporated to 50 ml. The dissolved polymer was precipitated with an excess of acetone and isolated on a D1 frit. This "(amorphous) ether-soluble fraction" was dried under reduced pressure.

3. Random Copolymer

Random copolymerizations were carried out in a 10 l reactor charged with 3.5 l of liquid propene. The reactors were blanketed with nitrogen prior to filling. A 20% strength by weight solution of triethylaluminum in Exxsol (from Witco) was introduced into the reactors and the mixtures were stirred at 30° C. for 15 minutes. A suspension of the respective catalyst in 20 ml of Exxsol was introduced into the reactors. Ethylene pressure was added (totally 160 g of ethylene). The reactor temperature was increased to 65° C. and held at this temperature for 60 minutes. Polymerization Pressure 32 bar was kept by continuous feeding of ethylene (amount fed was 47 g). The polymerizations were stopped by venting the reactor. The polymers were dried overnight under reduced pressure before being analyzed.

Determination of the Melting Point:

The melting point $T_m$ was determined by DSC measurement in accordance with ISO standard 3146 by means of a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the enthalpy versus temperature curve measured in the second heating phase displayed a maximum.

Determination of the Viscosity Number (I.V.):

The viscosity number was determined in decalin at 135° C. in an Ubbelohde viscometer PVS 1 using a measuring head S 5 (both from Lauda). To prepare the sample, 20 mg of polymer were dissolved in 20 ml of decalin at 135° C. over a period of 2 hours. 15 ml of the solution were introduced into the viscometer, and the instrument carried out at least three flow time measurements until a consistent result was obtained. The I.V. was calculated from the running times in accordance with the equation $I.V.=(t/t_0-1)*1/c$, where t is the mean of the flow time of the solution, $t_0$ is the mean of the flow time of the solvent, c is the concentration of the solution in g/ml.

Gel Permeation Chromatography:

The gel permeation chromatography (GPC) was carried out at 145° C. in 1,2,4-trichlorobenzene using a GPC apparatus 150C from Waters. The data were evaluated using the software Win-GPC from HS-Entwicklungsgesellschaft für wissenschaftliche Hard- und Software mbH, Ober-Hilbersheim. The columns were calibrated by means of polypropylene standards having molar masses from 100 to $10^7$ g/mol. Mass (weight) average ($M_w$) and number average ($M_n$) of the molar masses of the polymers were determined. The Q value is the ratio of mass average ($M_w$) to number average ($M_n$).

EXAMPLES

1. Dimethylsilanediyl(2,7-dimethyl-4-(4'-tert-butylphenyl)-1-indenyl)(2-isopropyl-4-(4'-tert-butylphenyl)-1-indenyl)zirconium dichloride (1)

1a Preparation of 2-chloro-5-methylpropiophenone (1a)

43.8 g (329 mmol) of aluminum chloride and 34.66 g (274 mmol) of 4-chlorotoluene were placed in a reaction vessel and admixed with 26.6 g (287 mmol) of propionyl chloride. Moderate HCl gas evolution occurred. The reaction mixture was stirred at 50° C. for four hours and was subsequently poured into a mixture of 350 ml of ice water and 35 ml of concentrated HCl. The aqueous phase was extracted twice with 200 ml each time of methylene chloride. The combined organic phase was washed with 200 ml of water, 200 ml of $NaHCO_3$ solution and NaCl solution and dried over $MgSO_4$. Removal of the solvent and drying in an oil pump vacuum gave 47.06 g of (1a).

$^1$H-NMR (400 MHz, $CDCl_3$): 7.60–7.10 (m, 3H, arom-H), 2.94 (m, 2H, $CH_2$—H), 2.32 (s, 3H, $CH_3$), 1.18 (t, 3H, $CH_3$).

1b Preparation of 2-chloro-5-methylmethacrylophenone (1b)

47.0 g (257 mmol) of 2-chloro-7-methylpropiophenone (1a) and 21.2 ml (765 mmol) of formaldehyd solution were placed in a reaction vessel and a solution of 10.3 g (257 mmol) of NaOH in 515 ml of water was added over a period of 30 minutes. The reaction mixture was stirred at 40° C. for two hours. The phases were subsequently separated and the aqueous phase was extracted twice with 200 ml of methylene chloride. The combined organic phases were washed with 200 ml aqueous HCl solution and subsequently dried over $MgSO_4$. Removal of the solvent and drying in an oil pump vacuum gave 47.37 g of (1b).

$^1$H-NMR (400 MHz, $CDCl_3$): 7.39–7.05 (m, 3H, arom-H), 5.97; 5.57 (dd, 2H, $CH_2$—H), 2.31 (s, 3H, $CH_3$), 2.02 (s, 3H, $CH_3$).

1c Preparation of 7-chloro-2,4-methyl-1-indanone (1c)

349 g of concentrated sulfuric acid were placed in a reaction vessel at 65° C. and 47.3 g (243 mmol) of 2-chloro-5-methylmethacrylophenone (1b) were added dropwise over a period of two hours, the mixture was stirred at 65° C. for another 30 minutes and then cooled to room temperature. The reaction mixture was poured into 800 g of ice water. The resulting brownish green suspension was extracted three times with 300 ml each time of diethyl ether. The combined organic phases were washed with 300 ml of $NaHCO_3$ solution, 300 ml of water and 300 ml of saturated NaCl solution and subsequently dried over $MgSO_4$. Removal of the solvent and drying in an oil pump vacuum gave 39.29 g of (1c).

$^1$H-NMR (400 MHz, $CDCl_3$): 7.50–7.00 (m, 2H, arom-H), 3.32, 3.21 (dd, 2H, $CH_2$—H), 2.70 (m, 1H, CH—H), 2.28 (s, 3H, $CH_3$), 1.30 (d, 3H, $CH_3$).

1d Preparation of 2,4-dimethyl-7-(4'-tert-butylphenyl)-1-indanone (1d)

13.4 (68.8 mmol) of 7-chloro-2,4-dimethyl-1-indanone (1c), 14.71 g (82.6 mmol) of 4-tert-butylphenylboronic acid, 16.05 g (151 mmol) of sodium carbonate, 188 ml of ethylene glycol and 30.7 ml of water were placed under a protective gas atmosphere in a reaction vessel and heated to 80° C. While stirring vigorously, a freshly prepared catalyst solution of 77 mg (0.343 mmol) of palladium acetate, 1.7 ml (1.01 mmol) of an aqueous TPPTS solution (0.6 molar) in 25 ml of water was added to the reaction components and the reaction mixture was refluxed for 3 hours until the reaction was complete. After cooling to room temperature, the ethylene glycol phase was extracted three times with a total of 900 ml of toluene. The combined toluene phases were washed twice with a total of 250 ml of sodium chloride solution and dried over 150 g of sodium sulfate. Removal of the solvent, drying of the residue and subsequent distillation in an oil pump vacuum gave 18.59 g of (1d).

$^1$H-NMR (400 MHz, $CDCl_3$): 7.39–7.19 (m, 6H, arom-H), 3.30 (dd, 1H, $CH_2$—H), 2.68 (m, 1H, CH—H), 2.60 (dd, 1H, $CH_2$—H), 2.35 (s, 3H, $CH_3$), 1.34 (s, 9H, tert-butyl-H), 1.27 (d, 3H, $CH_3$).

1e Preparation of 2,7-dimethyl-4-(4'-tert-butylphenyl)indene (1e)

2.09 g (55.3 mmol) of sodium borohydride and 18.59 g (55.3 mmol) of 2,4-dimethyl-7-(4'-tert-butylphenyl)-1-indanone (1d) together with 51 ml of toluene were placed in a reaction vessel. At 50° C., 9.8 ml of methanol were added slowly and the reaction mixture was stirred at 50° C. for 3 hours. After cooling to room temperature, 35 ml of 2 N sulfuric acid were added and the mixture was stirred for 30 minutes. After phase separation, the organic phase was washed twice with a total of 60 ml of 2 N sulfuric acid, most of the solvent was removed and the residue was taken up in 200 ml of toluene and admixed with 0.2 g of p-toluenesulfonic acid. Water was distilled off from this reaction mixture by refluxing for 1.5 hours on a water separator until reaction was complete. The reaction mixture was washed once with 100 ml of saturated sodium hydrogen carbonate solution and dried over magnesium sulfate. After removal of the solvent, the residue was dried in an oil pump vacuum. This gave 16.8 g of the desired product (1e).

$^1$H-NMR (400 MHz, CDCl$_3$): 7.50–6.97 (m, 6H, arom-H), 6.70 (s, 1H, olefin-H), 3.24 (s, 2H, CH$_2$—H), 2.35 (s, 3H, CH$_3$), 2.15 (s, 3H, CH$_3$), 1.36 (s, 9H, tert-butyl-H).

1f Preparation of dimethylsilanediyl(2-isopropyl-4-(4'-tert-butylphenyl)-1-indene)-(2,7-dimethyl-4-(4'-tert-butylphenyl)-1-indene) (1f)

8.0 g (26 mmol) of 2,7-dimethyl-4-(4'-tert-butylphenyl) indene (1e) together with 82 ml toluene and 3.8 ml of THF were placed in a reaction vessel and, at room temperature, 11.0 ml of butyllithium solution (2.68 M in toluene) were added all at once. After this addition, the mixture was heated to 80° C. and stirred at this temperature for 1 hour. After cooling to room temperature, the reaction mixture was added over a period of 1 hour to a solution of 11.88 g (26 mmol) of 2-isopropyl-7-(4'-tert-butylphenyl)-1-indenedimethylchlorosilane (prepared by a method analogous to that in WO 01/48034, Example 5, page 58) and the resulting mixture was stirred overnight at room temperature. 60 ml of water were added, the phases were separated, the organic phase was washed with 100 ml of water and the combined aqueous phases were extracted twice with a total of 100 ml of toluene. The combined organic phases were dried over magnesium sulfate. After removal of the solvent, the residue was dried in an oil pump vacuum to give 18.53 g of (1f).

$^1$H-NMR (400 MHz, CDCl$_3$): 7.5–7.1 (m, 13H, arom-H), 6.71, 6.62 (each s, each 1H, olefin-H-indene), 3.31, 3.35 (each s, each 1H, CH$_2$—H), 2.65 (m, 1H, CH-isopropyl), 2.45, 2.34 (s, 3H, CH$_3$—H), 1.35, 1.33 (each s, each 9H, tert-butyl), 1.15 (d, 6H, isopropyl-CH$_3$), –0.07, –0.7 (each d, each 3H, Si—CH$_3$).

1 Preparation of dimethylsilanediyl(2-isopropyl-4-(4'-tert-butylphenyl)-1-indenyl)(2,7-dimethyl-4-(4'-tert-butylphenyl)indenyl)zirconium dichloride (1)

5 g (7.2 mmol) of (1f) together with 50 ml of diethyl ether were placed in a reaction vessel and admixed at room temperature with 5.8 ml of butyllithium solution (2.68 M in toluene). After this addition, the mixture was stirred overnight at room temperature. The reaction mixture was cooled to 0° C., and 1.68 g (7.2 mmol) of zirconium tetrachloride were added a little at a time. The reaction mixture was stirred at room temperature for 2 hours. The orange solid which had precipitated was then filtered off via a G3 frit and washed twice with 10 ml each time of Et$_2$O. The orange residue on the frit was dried in an oil pump vacuum to give 2.81 g of complex (1). Recrystallization of the crude complex (1) from toluene gave 0.88 g purified complex (1) in a rac:meso ratio of 20:1. The $^1$H-NMR signals of the rac-complex were determined.

$^1$H-NMR (400 MHz, CDCl$_3$): 1.041 (d, 6.68 Hz, 3H, i-Pr), 1.105 (d, 6.71 Hz, 3H, i-Pr), 1.333 (s, 9H, t-Bu), 1.337 (s, 15H, t-Bu+Me$_2$-Si), 2.239 (s, 3H, CH$_3$), 2.364 (s, 3H, CH$_3$), 3.3 (septet, 1H, i-Pr), 6.923 (s, 1H), 7.017 (s, 1H), 7.1–7.7 (13H, aromatic)

2. Dimethylsilanediyl(2-isopropyl-4-(4'-tert-butylphenyl)-1-indenyl)(2-ethyl-7-methyl-4-(4'-tert-butylphenyl)indenyl)zirconium dichloride (2)

2a Preparation of 2-chloro-5-methylbutyrophenone (2a)

Using a method analogous to the preparation of (1a), 187.1 g (1.4 mol) of aluminum chloride and 177.6 g (1.4 mol) of 4-chlorotoluene were reacted with 149.5 (1.4 mol) of butyryl chloride. 318 g of (2a) were obtained as crude product and were reacted further without additional purification.

2b Preparation of 7-chloro-2-ethyl-4-methyl-1-indanone (2b)

217.5 g (1.11 mol) of 2-chloro-5-methylbutyrophenone (2a) and 325.6 ml (2.32 mol) of urotropin were placed in a reaction vessel, and 282 ml (6.27 mol) of acetic anhydride were added dropwise over a period of 70 minutes. The reaction mixture was stirred at 80° C. for 3.5 hours. 250 ml of water and 527 g of NaOH were subsequently added. After cooling to room temperature, the phases were separated and the aqueous phase was extracted three times with a total of 1500 ml of methylene chloride. The combined organic phases were washed once with 1000 ml of aqueous HCl solution and evaporated to a volume of 370 ml. This solution was added dropwise to 1.84 kg of concentrated sulfuric acid at 70° C. over a period of 2.5 hours, with the temperature of the sulfuric acid solution being maintained at 70° C. After cooling to room temperature, the sulfuric acid solution was carefully poured onto 3 kg of ice, the sulfuric acid solution was extracted three times with a total of 2.5 l of dichloromethane, the combined organic phases were washed with 600 g of saturated NaHCO$_3$ solution and 300 ml of water and the organic phase was dried over MgSO$_4$. Removal of the solvent and drying in an oil pump vacuum gave 205 g of the desired product (2b).

2c Preparation of 2 ethyl-4-methyl-7-(4'-tert-butylphenyl)-1-indanone (2c)

Using a method analogous to Example 1d, 29.0 g (138.96 mmol) of 7-chloro-2-ethyl-4-methyl-1-indanone (1b), 29.7 g (166.8 mmol) of 4-tert-butylphenylboronic acid, 36.8 g (347.3 mmol) of sodium carbonate, 300 ml of ethylene glycol and 40 ml of water were reacted at 80° C. in the presence of a freshly prepared catalyst solution of 156 mg (0.695 mmol) of palladium acetate, 3.5 ml (2.08 mmol) of an aqueous TPPTS solution (0.6 molar) in 19 ml of water. 45.00 g of (2c) were isolated.

$^1$H-NMR (400 MHz, CDCl$_3$): 7.41–7.18 (m, 6H, arom-H), 3.23 (dd, 1H, CH$_2$—H), 2.68 (dd, 1H, CH$_2$—H), 2.57 (m, 1H, CH—H), 2.36 (s, 3H, CH$_3$), 1.96 (q, 2H, CH$_2$), 1.34 (s, 9H, tert-butyl-H), 1.06 (t, 3H, CH$_3$).

2d Preparation of 2-ethyl-7-methyl-4-(4'-tert-butylphenyl) indene (2d)

Using a method analogous to Example 1e, 6.1 g (161.3 mmol) of sodium borohydride and 45.00 g (146.84 mmol) of (2c) in 100 ml toluene were reacted with 25.7 ml of methanol, and the indanol was isolated after appropriate work-up. The crude indanol was in turn converted by a method analogous to Example 1e in the presence of 200 ml of toluene and 0.3 g of p-toluenesulfonic acid into the indene (2d), of which 39.8 g were obtained.

$^1$H-NMR (400 MHz, CDCl$_3$): 7.48–7.01 (m, 6H, arom-H), 6.74 (s, 1H, olefin-H), 3.28 (s, 2H, CH$_2$—H), 2.54 (q, 2H, CH$_2$), 2.37 (s, 3H, CH$_3$), 1.38 (s, 9H, tert-butyl-H), 1.21 (t, 3H, CH$_3$).

2e Preparation of dimethylsilanediyl(2-isopropyl-4-(4'-tert-butylphenyl)-1-indene)-(2-ethyl-7-methyl-4-(4'-tert-butylphenyl)-1-indene) (2e)

Using a method analogous to Example 1f, 10.0 g (26 mmol) of 2-ethyl-7-methyl-4-(4'-tert-butylphenyl)indene in 99 ml of toluene and 4.6 ml of THF were deprotonated with 13.2 ml of buthyllithium solution (2.68 M in toluene) and reacted with a solution of 12.0 g (26 mmol) of 2-isopropyl- 7-(4'-tert-butylphenyl)-1-indenedimethylchlorosilane in 33 ml of toluene. After work-up, 20.81 g of the bisindenyl ligand (2e) were isolated.

$^1$H-NMR (400 MHz, CDCl$_3$): 7.48–7.01 (m, 13H, arom-H), 6.70, 6.62 (each s, each 1H, olefin-H-indene), 3.41, 3.26 (each s, each 1H, CH$_2$—H), 2.6–2.5 (m, 3H, CH-isopropyl and CH$_2$-ethyl), 2.35 (s, 3H, CH$_3$—H), 1.37, 1.35 (each s, each 9H, tert-butyl), 1.19 (t, 3H, CH$_3$), 1.15 (d, 6H, isopropyl-CH$_3$), 0.04–0.7 (each d, each 3H, Si—CH$_3$).

2 Preparation of dimethylsilanediyl(2-isopropyl-4-(4'-tert-butylphenyl)-1-indenyl)(2-ethyl-7-methyl-4-(4'-tert-butylphenyl)indenyl)zirconium dichloride (2)

Using a method analogous to Example 1, 2 g (2.61 mmol) of (2e) in 20 ml of diethyl ether were admixed with 2.1 ml of butyllithium solution (2.68 M in toluene) and subsequently reacted with 0.61 g (2.61 mmol) zirconium tetrachloride. The orange complex was isolated and washed twice with 10 ml of toluene. The residue was dried in an oil pump vacuum. Compound (2) was obtained in a yield of 0.76 g.

3 Preparation of dimethylsilanediyl(2,5,6,7-tetramethyl-4-(4'-tert-butylphenyl)-1-indenyl)(2-isopropyl-4-(4'-tert-butylphenyl)-1-indenyl)zirconium dichloride (3)

3a Preparation of 2-bromo-3,4,5-trimethylpropiophenone (3a)

37 g (275 mmol) of aluminum chloride in 300 mL of dehydrated methylene chloride and 41 g (195 mmol) of 1-bromo-2,3,4-trimethylbenzene (synthesized by a procedure of the literature S. Kajigaeshi et.al. Bull. Chem. Soc. Jpn., 62, 439 (1989)) were placed in a reaction vessel. 21 g (222 mmol) of propionyl chloride in 200 ml of dehydrated methylene chloride was added dropwise at −15° C. and stirred for 2.5 hours and the reaction mixture was subsequently poured into a mixture of 350 ml of ice water and 35 ml of concentrated hydrochloric acid. The aqueous phase was extracted twice with 200 ml each time of methylene chloride. The combined organic phase was washed with 200 ml of water, 200 ml of NaHCO$_3$ solution and NaCl solution and dried over MgSO$_4$. Removal of the solvent and drying in an oil pump vacuum gave 50.8 g of (3a). GC-MS: M$^+$=254

3b Preparation of 2-bromo-3,4,5-trimethylmethacrylophenone (3b)

48.0 g of 2-bormo-3,4,5-trimethylpropiophenone (3a) and 210 ml of formaldehyd solution were placed in a reaction vessel and a solution of 103 g of NaOH in 515 ml of water was added and stirred overnight. The phases were subsequently separated and the aqueous phase was extracted twice with 200 ml of methylene chloride. The combined organic phases were washed with 200 ml aqueous HCl solution and subsequently dried over MgSO$_4$. Removal of the solvent and drying in an oil pump vacuum gave 48 g of (3b).

3c Preparation of 4-bromo-2,5,6,7-tetramethyl-1-indanone (3c)

360 g of concentrated sulfuric acid were placed in a reaction vessel at 65° C. and 48 g (243 mmol) of 2-bromo-3,4,5-trimethylmethacrylophenone (3b) were added dropwise over a period of two hours, the mixture was stirred at 65° C. for another 30 minutes and then cooled to room temperature. The reaction mixture was poured into 800 g of ice water. The resulting brownish green suspension was extracted three times with 300 ml each time of diethyl ether. The combined organic phases were washed with 300 ml of NaHCO$_3$ solution, 300 ml of water and 300 ml of saturated NaCl solution and subsequently dried over MgSO$_4$. Removal of the solvent and purification by chromatography gave 18 g of (3c) as a white powder.

GC-MS: M$^+$=266+268

$^1$H-NMR (400 MHz, CDCl$_3$): 1.309 (d, 7.5 Hz, 3H, CH$_3$), 2.230 (s, 3H, CH$_3$), 2.345 (s, 3H, CH$_3$), 2.453 (s, 3H, CH$_3$), 2.50–2.55 (m, 1H), 2.67–2.72 (m, 1H), 3.19–3.25 (m, 1H)

3d Preparation of 2,5,6,7-tetramethyl-4-(4'-tert-butylphenyl)-1-indanone (3d)

17.5 g (65.5 mmol) of 4-bromo-2,5,6,7-tetramethyl-1-indanone (3c), 14 g (78.6 mmol) of 4-tert-butylphenylboronic acid, 17 g (160 mmol) of sodium carbonate, 200 ml of ethylene glycol and 35 ml of water were placed under a protective gas atmosphere in a reaction vessel and heated to 80° C. While stirring vigorously, a freshly prepared catalyst solution of 37 mg (0.16 mmol) of palladium acetate, 0.33 ml (0.6 mmol) of an aqueous TPPTS solution (0.6 molar) in 25 ml of water was added to the reaction components and the reaction mixture was refluxed for 3 hours until the reaction was complete. After cooling to room temperature, the ethylene glycol phase was extracted three times with a total of 900 ml of toluene. The combined toluene phases were washed twice with a total of 250 ml of sodium chloride solution and dried over 150 g of sodium sulfate. Removal of the solvent, drying of the residue and subsequent distillation in an oil pump vacuum gave 22 g of (3d).

3e Preparation of 2,5,6,7-tetramethyl-4-(4'-tert-butylphenyl)indene (3e)

5 g (131 mmol) of sodium borohydride and 21 g (80 mmol) of 2,5,6,7-tetramethyl-4-(4'-tert-butylphenyl)-1-indanone (3d) together with 200 ml of toluene were placed in a reaction vessel. At 50° C., 25 ml of methanol were added slowly and the reaction mixture was stirred at 50° C. for 3 hours. After cooling to room temperature, 35 ml of 2 N sulfuric acid were added and the mixture was stirred for 30 minutes. After phase separation, the organic phase was washed twice with a total of 60 ml of 2 N sulfuric acid, most of the solvent was removed and the residue was taken up in 200 ml of toluene and admixed with 0.2 g of p-toluenesulfonic acid. Water was distilled off from this reaction mixture by refluxing for 1.5 hours on a water separator until reaction was complete. The reaction mixture was washed once with 100 ml of saturated sodium hydrogen carbonate solution and dried over magnesium sulfate. After removal of the solvent, the residue was dried in an oil pump vacuum. Crude product was purified by recrystallization in heptane. This gave 9.0 g of (3e).

GC-MS: M$^+$=304

$^1$H-NMR (400 MHz, CDCl$_3$): 1.38 (s, 9H, t-Bu), 2.05 (s, 3H, Me), 2.15 (s, 3H, Me), 2.27 (s, 3H, Me), 2.35 (s, 3H, Me), 3.25 (s, 2H, allyl), 6.17 (s, 1H, vinyl), 7.16 (d, 2H, Ph), 7.23 (d, 2H, Ph)

3f Preparation of dimethylsilanediyl(2-isopropyl-4-(4'-tert-butylphenyl)-1-indene)-(2,5,6,7-tetramethyl-4-(4'-tert-butylphenyl)-1-indene) (3f)

8.96 g (29.4 mmol) of 2,5,6,7-tetramethyl-4-(4'-tert-butylphenyl)indene (3e) together with 72 mg (0.81 mmol) of cupper cyanide (I) and 250 mL of diethylether were placed in a reaction vessel and, at 0° C., 12.9 ml of butyllithium solution (2.5 M in toluene) were added all at once. After this addition, the mixture was heated to room temperature and stirred for 1 hour. After cooling to room temperature, the reaction mixture was added over a period of 1 hour to a solution of 12.4 g (32.4 mmol) of 2-isopropyl-7-(4'-tert-butylphenyl)-1-indenedimethylchlorosilane and the resulting mixture was stirred overnight at room temperature. 60 ml of water were added, the phases were separated, the organic phase was washed with 100 ml of water and the combined aqueous phases were extracted twice with a total of 100 ml of toluene. The combined organic phases were dried over magnesium sulfate. After removal of the solvent, the residue was dried in an oil pump vacuum to give 17.4 g of (3f).

GC-MS: $M^+$=650

$^1$H-NMR (400 MHz, CDCl$_3$): −0.444, −0.309, −0.323, −0.223 (6H, CH$_3$—Si), 1.178 (d, 6.89 Hz, 3H, CH$_3$ of i-Pr), 1.37 (d, 6.67 Hz, 3H, CH$_3$ of i-Pr), 1.380 (9H, t-Bu), 1.389 (9H, t-Bu), 1.547 (3H, CH$_3$), 2.135 (3H, CH$_3$), 2.238 (3H, CH$_3$), 2.283 (3H, CH$_3$), 3.0 (septet, 1H, i-Pr), 3.84, 3.94, 4.1 (2H, allyl), 6.245 (1H, vinyl), 3.84 (1H, vinyl), 7.0–7.5 (11H, aromatic)

3 Preparation of dimethylsilanediyl(2-isopropyl-4-(4'-tert-butylphenyl)-1-indenyl)(2,5,6,7-tetramethyl-4-(4'-tert-butylphenyl)indenyl)zirconium dichloride (3)

6.8 g (10.4 mmol) of (3f) together with 50 ml of diethyl ether and 350 ml of toluene were placed in a reaction vessel and admixed at room temperature with 8.32 ml of butyllithium solution (2.5 M in toluene). After this addition, the mixture was stirred overnight at room temperature. The reaction mixture was cooled to 0° C., and 2.43 g (10.4 mmol) of zirconium tetrachloride were added a little at a time. The reaction mixture was stirred at room temperature for 2 hours. The orange solid which had precipitated was then filtered off via a G3 frit and washed twice with 10 ml each time of Et$_2$O. The orange residue on the frit was dried in an oil pump vacuum to give 3.7 g of complex (3). 3.7 g of isolated complex (3) were suspended in 100 ml n-pentane and the solid was filtered off. The yellow residue was dried in an oil pump vaccum to give 2.3 g of purified complex (3) having a rac:meso ratio of 9:1 determined by protone-NMR.

$^1$H-NMR (400 MHz, CDCl$_3$): 0.835 (d, 6.96 Hz, 3H, CH$_3$ of i-Pr), 0.987 (d, 6.52 Hz, 3H, CH$_3$ of i-Pr), 1.246 (s, 9H, t-Bu), 1.251 (s, 9H, t-Bu), 1.256 (s, 3H, CH$_3$—Si), 1.283 (s, 3H, CH$_3$—Si), 2.120 (s, 3H, CH$_3$), 2.127 (s, 6H, 2 CH$_3$), 2.492 (s, 3H, CH$_3$), 2.98–3.04 (septet, 1H, i-Pr), 6.390 (s, 1H), 6.880 (s, 1H), 6.8–7.6 (11H, aromatic H)

The following metallocenes were used in the polymerization experiments:

Metallocene (MC) No. Structure

1 Me$_2$Si(2-$^i$Pr-4-(p-$^t$-Bu-Ph)-1-Ind)(2,7-Me$_2$-4-(p-$^t$Bu-Ph)-1-Ind)ZrCl$_2$ (rac/meso: 20:1)

2 Me$_2$Si(2-$^i$Pr-4-(p-$^t$Bu-Ph)-1-Ind)(2-Et-7-Me-4-(p-$^t$Bu-Ph)-1-Ind)ZrCl$_2$ (rac/meso: 1:1)

3 Me$_2$Si(2-$^i$Pr-4-(p-$^t$Bu-Ph)-1-Ind)(2,5,6,7-Me$_4$-4-(p-$^t$Bu-Ph)-1-Ind)ZrCl$_2$ (rac/meso: 9:1)

c 1 Me$_2$Si(2-$^i$Pr-4-(p-$^t$Bu-Ph)-1-Ind)(2-Me-4-(p-$^t$Bu-Ph)-1-Ind)ZrCl$_2$ (rac/meso: 20:1)

c 2 Me$_2$Si(2-$^c$Hex-4-(p-$^t$Bu-Ph)-1-Ind)(2-Me-4-(p-$^t$Bu-Ph)-1-Ind)ZrCl$_2$ (rac/meso: 4.6:1)

c 3 Me$_2$Si(2-$^i$Pr-4-(p-$^t$Bu-Ph)-1-Ind)(2-Me-4-(1-Naph)-1-Ind)ZrCl$_2$ (rac/meso: 1:1)

c 4 Me$_2$Si(2-$^i$Pr-4-(p-$^t$Bu-Ph)-1-Ind)(2-Et-4-(p-$^t$Bu-Ph)-1-Ind)ZrCl$_2$ (rac/meso: 1:1)

1. Homopolymerizations and polymer analysis results.

| Example | MC No. | Amount | Propylene | H$_2$ | Activity | m.p | I.V. | Mw | Q |
| --- | --- | --- | --- | --- | --- | --- | --- | --- | --- |
| P 1 | 1 | 1000 mg | 3 l | no | 0.80 | 157.1 | 2.98 | 319 | 2.0 |
| P 2 | 1 | 250 mg | 3 l | yes | 2.00 | 157.7 | 0.90 | 96 | 1.9 |
| P 3 | 2 | 500 mg | 3 l | no | 0.46 | 159 | | 274 | |
| P 4 | 3 | 700 mg | 3.5 l | no | 0.19 | 157.0 | 3.71 | 580 | 2.5 |
| cP 1 | c 1 | 1500 mg | 10 l | no | 1.37 | 155.4 | 2.85 | 260 | 3.6 |
| cP 2 | c 1 | 800 mg | 10 l | yes | 3.41 | 156.4 | 0.93 | 85 | 3.2 |
| cP 3 | c 2 | 1500 mg | 10 l | no | 0.37 | 153.7 | 3.85 | 421 | 2.8 |
| cP 4 | c 2 | 250 mg | 3 l | yes | 2.20 | 154.4 | 1.30 | 113 | 2.3 |
| cP 5 | c 3 | 1500 mg | 10 l | no | 0.28 | 155.7 | 4.36 | 356 | 2.2 |
| cP 6 | c 3 | 250 mg | 3 l | yes | 0.36 | 156.1 | 1.17 | 121 | 4.7 |
| cP 7 | c 4 | 1500 mg | 3 l | no | 0.37 | 156.1 | 4.18 | | |

Units and abbreviations: activity: kg/(g*h); melting point (m.p.): ° C.; viscosity number (I.V.): dl/g; weight average molar mass (Mw): 10$^3$ g/mol; polydispersity: Q=Mw/Mn Microstructure of homopolymers as determined by $^{13}$C-NMR spectroscopy

| Example | E | H | mmrm | mmmm |
| --- | --- | --- | --- | --- |
| P 1 | 0.22 | 0.04 | 0.11 | 98.14 |
| P 2 | 0.21 | 0.05 | 0.08 | 98.31 |
| cP 1 | 0.32 | 0.08 | 0.36 | 96.17 |
| cP 2 | 0.41 | 0.00 | 0.36 | 96.17 |

All units in %; abbreviations: E: erythro-2,1-regio defects; H: 3,1-regio defects; mrrm: stereo defects; mmmm: mmmm pentads calculated from 100−5*mrrm−5*E−5*H 2. Copolymerizations for impact copolymers.

| Example | MC No. | Amount | Activity [kg/(g*h)] |
| --- | --- | --- | --- |
| P 5 | 1 | 1 500 mg | 0.53 |
| cP 8 | c1 | 1 500 mg | 1.41 |
| cP 9 | c2 | 1 600 mg | 0.89 |
| cP 10 | c3 | 1 500 mg | 0.17 |

Triad distribution at P 5: PPP: 73.69%; PPE: 14.12%; EPE: 1.30%; PQP: 0.06%; EQP: 0.02%; PEQ: 0.02%; PEP: 1.12%; PEE: 3.01%; EEE: 0.59%. Abbreviations: P: regioregular propylene, Q: regioirregular propylene; E: ethylene; PEQ is the series formed by an ethylene insertion after a regioirregular propylene insertion.

Fractionation of the polymer blends:

|  | Crystalline fraction | | Ether-insoluble fraction | | | Ether-soluble fraction | |
|---|---|---|---|---|---|---|---|
| Example | Proportion | I.V. | Proportion | I.V. | C2 content | Proportion | I.V. |
| P 5 | 30.0 | 3.40 | 65.7 | 5.22 | 10.4 | 4.3 | 3.05 |
| cP 8 | 31.1 | 2.92 | 68.5 | 3.31 | 8.2 | 0.4 | 0.51 |
| cP 9 | 17.0 | 3.13 | 79.2 | 4.11 | 9.1 | 3.9 | 1.00 |
| cP 10 | 36.2 | 4.48 | 59.8 | 4.70 | 9.7 | 10.0 | 0.56 |

Units: proportion, C2 content: % by weight; I.V.: dl/g.

The ether-insoluble fraction of P 5 has, on the basis of GPC, an $M_w$ of $652*10^3$ g/mol and a polydispersity of 2.4.

3. Copolymerization for randomcopolymers

| Ex. | MC No. | Amount/ [mg] | Propene/ [l] | Activity/ [kg/gh] | I.V./ [dl/g] | Mw/ [g/mol] | Q | C2 [wt %] | m.p. [° C.] |
|---|---|---|---|---|---|---|---|---|---|
| P 6 | 1 | 207 | 3.5 | 5.4 | 3.71 | 608000 | 2.7 | 3.4 | 123 |
| P 7 | 3 | 605 | 3.5 | 0.8 | 5.40 | 1055000 | 3.5 | 4.1 | 118 |
| cP 11 | c 1 | 218 | 3.5 | 4.7 | 2.86 | 411000 | 2.3 | 3.3 | 125 |

We claim:

1. An organometallic transition metal compound of the formula (I)

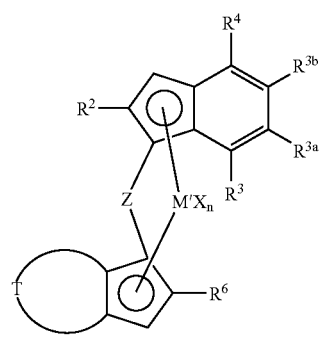

(I)

where $M^1$ is an element of group 3, 4, 5 or 6 of the Periodic Table of the Elements or the lanthanides, X are identical or different or different and are each halogen, hydrogen, $C_1$–$C_{20}$-alkyl, $C_2$–$C_{20}$-alkenyl, $C_6$–$C_{22}$-aryl, alkylaryl or arylalkyl having from 1 to 10 carbon atoms in the alkyl part and from 6 to 22 carbon atoms in the aryl part, —$OR^5$ or —$NR^5R^6$, where two radicals X may also be joined to one another or two radicals X may together form a substituted or unsubstituted diene ligand, in particular a 1,3-diene ligand, where $R^5$ and $R^6$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 22 carbon atoms in the aryl radical, n is a natural number from 1 to 4 which is equal to the oxidation number of $M^1$ minus 2, $R^1$ is a $C_2$–$C_{40}$ radical which is branched in the α position $R^2$ is hydrogen or a $C_1$–$C_{40}$ radical which is unbranched in the α position, $R^3$, $R^{3a}$ and $R^{3b}$ are identical or different and are each hydrogen or a $C_1$–$C_{40}$ radical, where $R^3$ is not hydrogen, $R^4$ is a substituted or unsubstituted $C_6$–$C_{40}$-aryl radical or $C_2$–$C_{40}$-heteroaromatic radical containing at least one heteroatom selected from the group consisting of O, N, S and P, T is a divalent $C_1$–$C_{40}$ group which together with the cyclopentadienyl ring forms a further saturated or unsaturated ring system having a ring size of from 5 to 12 atoms, where T may contain the heteroatoms Si, Ge, N, P, O or S within the ring system fused onto the cyclopentadienyl ring, and Z is a bridge consisting of a divalent atom or a divalent group.

2. A organometallic transition metal compound of the formula (I) as claimed in claim 1, wherein $M^1$ is an element of group 4 of the Periodic Table of the Elements, n is 2, $R^{3a}$ is hydrogen, $R^{3b}$ is hydrogen, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (I).

3. An organometallic transition metal compound of the formula (I) as claimed in claim 1, wherein $M^1$ is an element of group 4 of the Periodic Table of Elements, n is 2, $R^3$ is a $C_1$–$C_{40}$ radical, $R^{3a}$, $R^{3b}$ are identical or different and are each hydrogen or a $C_1$–$C_{40}$ radical, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (I).

4. A catalyst system comprising at least one organometallic transition metal compound as claimed in claim 1 and at least one cocatalyst.

5. A catalyst system as claimed in claim 4 which further comprises a support.

6. A process for preparing polyolefins by polymerization or copolymerization of at least one olefin in the presence of a catalyst system as claimed in claim 4.

7. A process for preparing polypropylene/propylene-ethylene copolymer mixtures in the presence of a catalyst system as claimed in claim 4.

8. A biscyclopentadienyl ligand system of the formula (II)

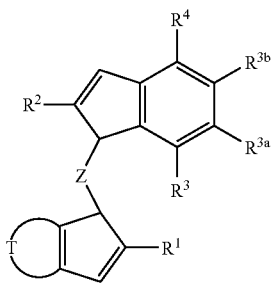

(II)

or its double bond isomers
where $R^1$ is a $C_2$–$C_{40}$ radical which is branched in the α position $R^2$ is hydrogen or a $C_1$–$C_{40}$ radical which may be branched or unbranched in the α position, $R^3$, $R^{3a}$ and $R^{3b}$ are identical or different and are each hydrogen or a $C_1$–$C_{40}$ radical, where $R^3$ is not hydrogen, $R^4$ is a substituted or unsubstituted $C_6$–$C_{40}$-aryl radical or $C_1$–$C_{40}$-heteroaromatic radical containing at least one heteroatom selected from the group consisting of O, N, S and P, T is a divalent $C_1$–$C_{40}$ group which together with the cyclopentadienyl ring forms a further saturated or unsaturated ring system having a ring size of from 5 to 12 atoms, where T may contain the heteroatoms Si, Ge, N, P, O or S within the ring system fused onto the cyclopentadienyl ring, and Z is a bridge consisting of a divalent atom or a divalent group.

9. A biscyclopentadienyl ligand system of the formula (II) as claimed in claim 8, wherein $R^{3a}$ is hydrogen, $R^{3b}$ is hydrogen, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (II).

10. A biscyclopentadienyl ligand system of the formula (II) as claimed in claim 8, wherein $R^3$ is a $C_1$–$C_{40}$ radical $R^{3a}$, $R^{3b}$ are identical or different and are each hydrogen or a $C_1$–$C_{40}$ radical, T is a divalent $C_1$–$C_{40}$ group which together with the cyclopentadienyl ring forms a further saturated or unsaturated ring system having a ring size of from 5 to 7 atoms, where T may contain the heteroatoms N or S within the ring system fused onto the cyclopentadienyl ring, and the other variables are as defined under formula (II).

11. An organometallic transition metal compound comprising the biscyclopentadienyl ligand system as claimed in claim 8.

* * * * *